(12) United States Patent
Rorick et al.

(10) Patent No.: US 12,127,943 B2
(45) Date of Patent: *Oct. 29, 2024

(54) CARTILAGE MOSAIC COMPOSITIONS AND METHODS

(71) Applicant: AlloSource, Centennial, CO (US)

(72) Inventors: Carolyn Barrett Rorick, Denver, CO (US); Yaling Shi, Larkspur, CO (US)

(73) Assignee: AlloSource, Centennial, CO (US)

( * ) Notice: Subject to any disclaimer, the term of this patent is extended or adjusted under 35 U.S.C. 154(b) by 346 days.

This patent is subject to a terminal disclaimer.

(21) Appl. No.: 17/388,388

(22) Filed: Jul. 29, 2021

(65) Prior Publication Data

US 2021/0353422 A1 Nov. 18, 2021

Related U.S. Application Data

(63) Continuation of application No. 16/459,136, filed on Jul. 1, 2019, now Pat. No. 11,123,193, which is a continuation of application No. 15/608,679, filed on May 30, 2017, now Pat. No. 10,335,281, which is a continuation of application No. 14/875,258, filed on
(Continued)

(51) Int. Cl.
*A61F 2/30* (2006.01)
*A61L 27/36* (2006.01)

(52) U.S. Cl.
CPC ...... *A61F 2/30756* (2013.01); *A61L 27/3608* (2013.01); *A61L 27/3612* (2013.01); *A61F 2002/30113* (2013.01); *A61F 2002/30153* (2013.01); *A61F 2002/30154* (2013.01); *A61F 2002/30759* (2013.01); *A61F 2002/30784* (2013.01); *A61F 2002/3097* (2013.01);
(Continued)

(58) Field of Classification Search
CPC ........ A61F 2/30756; A61F 2002/30113; A61F 2002/30153; A61F 2002/30784; A61F 2002/3097; A61F 2240/002; A61F 2310/00359; A61F 2310/00371; A61L 27/3608

See application file for complete search history.

(56) References Cited

U.S. PATENT DOCUMENTS

| | | | |
|---|---|---|---|
| 4,627,853 | A | 12/1986 | Campbell et al. |
| 4,642,120 | A | 2/1987 | Itay et al. |

(Continued)

FOREIGN PATENT DOCUMENTS

| | | |
|---|---|---|
| EP | 1 712 205 A1 | 7/2012 |
| WO | 2005058207 | 6/2005 |

(Continued)

OTHER PUBLICATIONS

Abazari et al., "Cryopreservation of articular cartilage", Cryobiology, vol. 66, pp. 201-209, Mar. 13, 2013.
(Continued)

*Primary Examiner* — Suzette J Gherbi
(74) *Attorney, Agent, or Firm* — Kilpatrick Townsend & Stockton LLP

(57) ABSTRACT

Compositions comprising a cartilage sheet comprising a plurality of interconnected cartilage tiles and a biocompatible carrier are provided. Methods of manufacturing cartilage compositions comprising a cartilage sheet comprising a plurality of interconnected cartilage tiles are also provided.

15 Claims, 24 Drawing Sheets

Related U.S. Application Data

Oct. 5, 2015, now Pat. No. 9,700,415, which is a continuation of application No. 14/187,093, filed on Feb. 21, 2014, now Pat. No. 9,186,253.

(60) Provisional application No. 61/768,190, filed on Feb. 22, 2013.

(52) U.S. Cl.
CPC .................. *A61F 2240/002* (2013.01); *A61F 2310/00359* (2013.01); *A61F 2310/00371* (2013.01)

(56) References Cited

U.S. PATENT DOCUMENTS

| | | | |
|---|---|---|---|
| 4,932,973 A * | 6/1990 | Gendler | A61F 2/30756 623/23.63 |
| 5,073,373 A | 12/1991 | O'Leary et al. | |
| 5,131,850 A | 7/1992 | Brockbank | |
| 5,284,655 A | 2/1994 | Bogdansky et al. | |
| 5,314,476 A | 5/1994 | Prewett et al. | |
| 5,405,390 A | 4/1995 | O'Leary et al. | |
| 5,439,684 A | 8/1995 | Prewett et al. | |
| 5,507,813 A | 4/1996 | Dowd et al. | |
| 5,510,396 A | 4/1996 | Prewett et al. | |
| 5,531,791 A | 7/1996 | Wolfinbarger | |
| 5,582,752 A | 12/1996 | Zair | |
| 5,676,146 A | 10/1997 | Scarborough | |
| 5,749,874 A | 5/1998 | Schwartz | |
| 5,755,791 A | 5/1998 | Whitson et al. | |
| 5,769,899 A | 6/1998 | Schwartz et al. | |
| 5,788,941 A | 8/1998 | Dalmasso et al. | |
| 5,895,426 A | 4/1999 | Scarborough et al. | |
| 5,899,939 A * | 5/1999 | Boyce | A61L 27/3608 523/113 |
| 5,968,096 A | 10/1999 | Whitson et al. | |
| 6,050,991 A | 4/2000 | Guillet | |
| 6,090,998 A | 7/2000 | Grooms et al. | |
| 6,180,606 B1 | 1/2001 | Chen et al. | |
| 6,200,347 B1 | 3/2001 | Anderson et al. | |
| 6,235,316 B1 | 5/2001 | Adkisson | |
| 6,280,437 B1 | 8/2001 | Pacala et al. | |
| 6,294,041 B1 | 9/2001 | Boyce et al. | |
| 6,294,187 B1 | 9/2001 | Boyce et al. | |
| 6,315,795 B1 | 11/2001 | Scarborough et al. | |
| 6,340,477 B1 | 1/2002 | Anderson | |
| 6,371,988 B1 | 4/2002 | Pafford et al. | |
| 6,436,138 B1 | 8/2002 | Dowd | |
| 6,478,825 B1 | 11/2002 | Winterbottom et al. | |
| 6,482,233 B1 | 11/2002 | Aebi et al. | |
| 6,511,509 B1 | 1/2003 | Ford et al. | |
| 6,514,514 B1 | 2/2003 | Atkinson et al. | |
| 6,541,024 B1 * | 4/2003 | Kadiyala | A61L 27/12 523/114 |
| 6,576,015 B2 | 6/2003 | Geistlich et al. | |
| 6,593,138 B1 | 7/2003 | Oliver et al. | |
| 6,607,524 B1 | 8/2003 | LaBudde et al. | |
| 6,616,698 B2 | 9/2003 | Scarborough | |
| 6,626,945 B2 | 9/2003 | Simon et al. | |
| 6,638,271 B2 | 10/2003 | Munnerlyn et al. | |
| 6,645,764 B1 | 11/2003 | Adkisson | |
| 6,652,593 B2 | 11/2003 | Boyer, II et al. | |
| 6,656,489 B1 * | 12/2003 | Mahmood | A61L 27/18 435/395 |
| 6,670,269 B2 | 12/2003 | Mashino | |
| 6,685,626 B2 | 2/2004 | Wironen | |
| 6,692,761 B2 | 2/2004 | Mahmood et al. | |
| 6,696,073 B2 | 2/2004 | Boyce et al. | |
| 6,712,822 B2 | 3/2004 | Re et al. | |
| 6,716,245 B2 | 4/2004 | Pasquet et al. | |
| 6,746,484 B1 | 6/2004 | Liu et al. | |
| 6,805,713 B1 | 10/2004 | Carter et al. | |
| 6,808,585 B2 | 10/2004 | Boyce et al. | |
| 6,855,169 B2 | 2/2005 | Boyer et al. | |
| 6,858,042 B2 | 2/2005 | Nadler et al. | |
| 6,863,694 B1 | 3/2005 | Boyce et al. | |
| 6,872,226 B2 | 3/2005 | Cali et al. | |
| 6,902,578 B1 | 6/2005 | Anderson et al. | |
| 6,911,045 B2 | 6/2005 | Shimp | |
| 7,018,412 B2 | 3/2006 | Ferreira et al. | |
| 7,048,765 B1 | 5/2006 | Grooms et al. | |
| 7,067,123 B2 | 6/2006 | Gomes et al. | |
| 7,115,146 B2 | 10/2006 | Boyer, II et al. | |
| 7,229,440 B2 | 6/2007 | Alden et al. | |
| 7,288,086 B1 | 10/2007 | Manvel et al. | |
| 7,316,822 B2 | 1/2008 | Binette et al. | |
| 7,335,381 B2 | 2/2008 | Malinin | |
| 7,338,495 B2 | 3/2008 | Adams | |
| 7,351,241 B2 | 4/2008 | Bendett et al. | |
| 7,361,195 B2 | 4/2008 | Schwartz et al. | |
| 7,371,409 B2 | 5/2008 | Petersen et al. | |
| 7,498,040 B2 | 3/2009 | Masinaei et al. | |
| 7,550,007 B2 | 6/2009 | Malinin | |
| 7,582,309 B2 | 9/2009 | Rosenberg et al. | |
| 7,608,113 B2 | 10/2009 | Boyer et al. | |
| 7,662,185 B2 | 2/2010 | Alfaro et al. | |
| RE41,286 E | 4/2010 | Atkinson et al. | |
| 7,753,963 B2 | 7/2010 | Boyer et al. | |
| 7,758,643 B2 | 7/2010 | Stone et al. | |
| 7,763,071 B2 | 7/2010 | Bianchi et al. | |
| 7,776,089 B2 | 8/2010 | Bianchi et al. | |
| 7,785,634 B2 | 8/2010 | Borden | |
| 7,807,458 B2 | 10/2010 | Schiller | |
| 7,815,926 B2 | 10/2010 | Syring et al. | |
| 7,824,711 B2 | 11/2010 | Kizer et al. | |
| 7,837,740 B2 | 11/2010 | Semler et al. | |
| 7,838,040 B2 | 11/2010 | Malinin | |
| 7,875,296 B2 | 1/2011 | Binette et al. | |
| 7,879,103 B2 | 2/2011 | Gertzman et al. | |
| 7,883,511 B2 | 2/2011 | Fernyhough | |
| RE42,208 E | 3/2011 | Truncale et al. | |
| 7,931,692 B2 | 4/2011 | Sybert et al. | |
| 8,002,813 B2 | 8/2011 | Scarborough et al. | |
| 8,002,837 B2 | 8/2011 | Stream et al. | |
| 8,012,206 B2 | 9/2011 | Schmieding | |
| 8,025,896 B2 | 9/2011 | Malaviya et al. | |
| 8,039,016 B2 | 10/2011 | Drapeau et al. | |
| 8,043,450 B2 | 10/2011 | Cali et al. | |
| 8,074,661 B2 | 12/2011 | Hutson et al. | |
| 8,083,755 B2 | 12/2011 | Mathisen et al. | |
| 8,133,421 B2 | 3/2012 | Boyce et al. | |
| 8,137,702 B2 | 3/2012 | Binette et al. | |
| 8,142,502 B2 | 3/2012 | Stone et al. | |
| 8,163,549 B2 | 4/2012 | Yao et al. | |
| 8,167,943 B2 | 5/2012 | Carter et al. | |
| 8,171,937 B2 | 5/2012 | Bendett et al. | |
| 8,173,162 B2 | 5/2012 | Vilei et al. | |
| 8,197,474 B2 | 6/2012 | Scarborough et al. | |
| 8,202,539 B2 | 6/2012 | Behnam et al. | |
| 8,221,500 B2 | 7/2012 | Truncale et al. | |
| 8,268,008 B2 | 9/2012 | Betz et al. | |
| 8,292,968 B2 | 10/2012 | Truncale et al. | |
| 8,309,106 B2 | 11/2012 | Masinaei et al. | |
| 8,318,212 B2 | 11/2012 | Malinin | |
| 8,343,229 B2 | 1/2013 | Coale | |
| 8,389,017 B1 | 3/2013 | Starling et al. | |
| 8,399,010 B2 | 3/2013 | McKay | |
| 8,403,991 B2 | 3/2013 | Ullrich, Jr. et al. | |
| 8,409,623 B2 | 4/2013 | Shim et al. | |
| 8,435,551 B2 | 5/2013 | Semler et al. | |
| 8,435,566 B2 | 5/2013 | Behnam et al. | |
| 8,480,757 B2 | 7/2013 | Gage et al. | |
| 8,496,970 B2 | 7/2013 | Binette et al. | |
| 8,497,121 B2 | 7/2013 | Yao et al. | |
| 8,506,632 B2 | 8/2013 | Ganem et al. | |
| 8,518,433 B2 | 8/2013 | Kizer et al. | |
| 8,524,268 B2 | 9/2013 | Kizer et al. | |
| 8,551,176 B2 | 10/2013 | Ullrich, Jr. et al. | |
| 8,563,040 B2 | 10/2013 | Marchosky | |
| 8,585,753 B2 | 11/2013 | Scanlon et al. | |
| 8,585,766 B2 | 11/2013 | Ullrich, Jr. et al. | |
| 8,641,775 B2 * | 2/2014 | Harmon | A61P 17/02 623/23.72 |

(56) References Cited

U.S. PATENT DOCUMENTS

| | | | |
|---|---|---|---|
| 8,652,214 B2 | 2/2014 | Fritz et al. | |
| 8,652,507 B2 | 2/2014 | Kizer et al. | |
| 8,722,075 B2 | 5/2014 | Shimp et al. | |
| 8,734,525 B2 | 5/2014 | Benham et al. | |
| 8,771,368 B2 | 7/2014 | McKay | |
| 8,859,007 B2 | 10/2014 | Carter et al. | |
| 8,865,199 B2 | 10/2014 | Coleman et al. | |
| 8,883,210 B1 | 11/2014 | Truncale et al. | |
| 8,945,535 B2 | 2/2015 | Steinwachs et al. | |
| 8,992,964 B2 | 3/2015 | Shelby et al. | |
| 9,005,646 B2 | 4/2015 | Masinaei et al. | |
| 9,029,077 B2 | 5/2015 | Song et al. | |
| 9,162,012 B2 | 10/2015 | Benham et al. | |
| 9,168,140 B2 | 10/2015 | Shi et al. | |
| 9,186,253 B2* | 11/2015 | Barrett | A61L 27/3608 |
| 9,186,380 B2* | 11/2015 | Shi | A61L 24/0005 |
| 9,408,875 B2 | 8/2016 | Masinaei et al. | |
| 9,603,710 B2 | 3/2017 | Shi et al. | |
| 9,700,415 B2* | 7/2017 | Barrett | A61P 19/04 |
| 10,335,281 B2* | 7/2019 | Barrett | A61L 27/3612 |
| 11,123,193 B2* | 9/2021 | Rorick | A61L 27/3608 |
| 2003/0055502 A1 | 3/2003 | Lang et al. | |
| 2003/0229400 A1 | 12/2003 | Masuda et al. | |
| 2004/0068256 A1 | 4/2004 | Rizoiu et al. | |
| 2004/0078090 A1* | 4/2004 | Binette | A61L 27/3604 435/395 |
| 2004/0230303 A1* | 11/2004 | Gomes | A61F 2/30756 623/16.11 |
| 2004/0249464 A1 | 12/2004 | Bindseil | |
| 2005/0288796 A1 | 12/2005 | Awad et al. | |
| 2006/0210643 A1 | 9/2006 | Truncale et al. | |
| 2006/0241756 A1 | 10/2006 | Fritz et al. | |
| 2006/0257908 A1 | 11/2006 | Rui et al. | |
| 2006/0275273 A1 | 12/2006 | Seyedin et al. | |
| 2007/0077237 A1 | 4/2007 | Damari et al. | |
| 2007/0179607 A1 | 8/2007 | Hodorek et al. | |
| 2007/0185231 A1 | 8/2007 | Liu et al. | |
| 2007/0233264 A1* | 10/2007 | Nycz | A61F 2/0095 623/23.57 |
| 2007/0265705 A1 | 11/2007 | Gaissmaier et al. | |
| 2007/0276506 A1* | 11/2007 | Troxel | A61F 2/28 8/94.11 |
| 2007/0299517 A1 | 12/2007 | Davisson et al. | |
| 2008/0004714 A1* | 1/2008 | Lieberman | A61B 17/58 623/23.76 |
| 2008/0014179 A1 | 1/2008 | Ferree | |
| 2008/0058953 A1 | 3/2008 | Scarborough | |
| 2008/0160496 A1 | 7/2008 | Rzepakovsky et al. | |
| 2008/0195216 A1 | 8/2008 | Phillip | |
| 2008/0249632 A1 | 10/2008 | Stone et al. | |
| 2008/0249638 A1 | 10/2008 | Asgari | |
| 2008/0269895 A1 | 10/2008 | Steinwachs et al. | |
| 2008/0305145 A1 | 12/2008 | Shelby et al. | |
| 2009/0010982 A1 | 1/2009 | Abrahams | |
| 2009/0024223 A1 | 1/2009 | Chen et al. | |
| 2009/0041730 A1 | 2/2009 | Barry et al. | |
| 2009/0291112 A1 | 11/2009 | Truncale et al. | |
| 2009/0312842 A1 | 12/2009 | Bursac et al. | |
| 2010/0049322 A1 | 2/2010 | McKay | |
| 2010/0124776 A1 | 5/2010 | Shi | |
| 2010/0168869 A1 | 7/2010 | Long et al. | |
| 2010/0196333 A1 | 8/2010 | Gaskins et al. | |
| 2010/0211173 A1 | 8/2010 | Bárdos et al. | |
| 2010/0241228 A1 | 9/2010 | Syring et al. | |
| 2010/0274362 A1 | 10/2010 | Yayon et al. | |
| 2011/0045044 A1 | 2/2011 | Masinaei et al. | |
| 2011/0052705 A1 | 3/2011 | Malinin | |
| 2011/0070271 A1 | 3/2011 | Truncale et al. | |
| 2011/0091517 A1 | 4/2011 | Binette et al. | |
| 2011/0177134 A1* | 7/2011 | Harmon | A61L 27/38 424/400 |
| 2011/0182961 A1 | 7/2011 | McKay | |
| 2011/0196355 A1 | 8/2011 | Mitchell et al. | |
| 2011/0262696 A1 | 10/2011 | Bayon | |
| 2011/0274729 A1 | 11/2011 | Collins | |
| 2011/0288568 A1 | 11/2011 | Capuzziello et al. | |
| 2012/0077181 A1* | 3/2012 | Schmidt | C12N 5/0657 435/255.2 |
| 2012/0082704 A1 | 4/2012 | Phillips et al. | |
| 2012/0107384 A1 | 5/2012 | Yao et al. | |
| 2012/0128641 A1 | 5/2012 | Austen | |
| 2012/0172991 A1* | 7/2012 | Bertele | A61F 2/447 623/17.16 |
| 2012/0215208 A1 | 8/2012 | Bendett et al. | |
| 2012/0226354 A1 | 9/2012 | Alleyne | |
| 2012/0230966 A1 | 9/2012 | Crawford et al. | |
| 2012/0244498 A1 | 9/2012 | Hall | |
| 2012/0251609 A1 | 10/2012 | Huang et al. | |
| 2012/0264211 A1 | 10/2012 | Jomha et al. | |
| 2012/0321878 A1 | 12/2012 | Landon et al. | |
| 2012/0330423 A1 | 12/2012 | Lin et al. | |
| 2013/0030528 A1 | 1/2013 | Chen et al. | |
| 2013/0035676 A1 | 2/2013 | Mitchell et al. | |
| 2013/0122095 A1 | 5/2013 | Kestler et al. | |
| 2013/0123937 A1 | 5/2013 | Jamiolkowski et al. | |
| 2013/0149294 A1 | 6/2013 | Rueger et al. | |
| 2013/0189338 A1 | 7/2013 | Drapeau et al. | |
| 2013/0197654 A1 | 8/2013 | Samuelson et al. | |
| 2013/0204392 A1 | 8/2013 | Law et al. | |
| 2013/0218125 A1* | 8/2013 | Stopek | B32B 27/12 604/93.01 |
| 2013/0344114 A1 | 12/2013 | Chang et al. | |
| 2013/0344601 A1 | 12/2013 | Soman et al. | |
| 2014/0012393 A1 | 1/2014 | Shin et al. | |
| 2014/0017283 A1 | 1/2014 | Yoo et al. | |
| 2014/0017292 A1 | 1/2014 | Yoo et al. | |
| 2014/0024115 A1 | 1/2014 | Bogdansky et al. | |
| 2014/0030309 A1 | 1/2014 | Yoo et al. | |
| 2014/0039621 A1 | 2/2014 | Gordon et al. | |
| 2014/0056865 A1* | 2/2014 | Samaniego | A61L 27/3687 424/549 |
| 2014/0058527 A1 | 2/2014 | Truncale et al. | |
| 2014/0091491 A1* | 4/2014 | Hung | A61L 27/3895 435/375 |
| 2014/0093543 A1 | 4/2014 | Morreale | |
| 2014/0099709 A1 | 4/2014 | Presnell et al. | |
| 2014/0121772 A1 | 5/2014 | Emerton et al. | |
| 2014/0134212 A1 | 5/2014 | Shi et al. | |
| 2014/0170232 A1 | 6/2014 | Shelby et al. | |
| 2014/0205674 A1 | 7/2014 | Wei | |
| 2014/0208980 A1 | 7/2014 | Song et al. | |
| 2014/0212471 A1 | 7/2014 | Drapeau et al. | |
| 2014/0212499 A1 | 7/2014 | Cooper et al. | |
| 2014/0212910 A1 | 7/2014 | Bhatia et al. | |
| 2014/0220142 A1 | 8/2014 | Song et al. | |
| 2014/0222159 A1 | 8/2014 | Bursac et al. | |
| 2014/0234272 A1 | 8/2014 | Vesey et al. | |
| 2014/0243993 A1 | 8/2014 | Barrett et al. | |
| 2014/0248324 A1* | 9/2014 | Grossin | A61L 27/20 623/23.72 |
| 2014/0255506 A1 | 9/2014 | Behnam et al. | |
| 2014/0271454 A1 | 9/2014 | L'Heureux et al. | |
| 2014/0271570 A1 | 9/2014 | Shi et al. | |
| 2014/0287960 A1 | 9/2014 | Shepherd et al. | |
| 2014/0314822 A1 | 10/2014 | Carter et al. | |
| 2014/0342013 A1 | 11/2014 | He et al. | |
| 2015/0004211 A1 | 1/2015 | Yoo et al. | |
| 2015/0004247 A1 | 1/2015 | Carter et al. | |
| 2015/0012107 A1 | 1/2015 | Koford et al. | |
| 2015/0017222 A1 | 1/2015 | Yoo et al. | |
| 2015/0093429 A1 | 4/2015 | Carter et al. | |
| 2015/0140057 A1 | 5/2015 | Yoo et al. | |
| 2015/0174295 A1 | 6/2015 | Woodell-May et al. | |
| 2015/0182667 A1 | 7/2015 | Guelcher et al. | |
| 2015/0216665 A1* | 8/2015 | Malinin | A61L 31/005 83/14 |
| 2015/0251361 A1 | 9/2015 | Meyer et al. | |
| 2015/0306278 A1 | 10/2015 | McKay | |
| 2016/0008134 A1* | 1/2016 | Shi | A61F 2/30756 435/402 |
| 2016/0022740 A1 | 1/2016 | Shi et al. | |
| 2016/0038290 A1 | 2/2016 | Barrett et al. | |

(56) References Cited

U.S. PATENT DOCUMENTS

| | | | | |
|---|---|---|---|---|
| 2016/0045640 | A1* | 2/2016 | Shi | A61L 27/3834 435/366 |
| 2016/0106885 | A1* | 4/2016 | Peretti | A61L 27/06 264/28 |
| 2016/0192621 | A1* | 7/2016 | Berner | A61B 10/0266 600/564 |
| 2020/0107935 | A1* | 4/2020 | Redl | A61L 27/3683 |

FOREIGN PATENT DOCUMENTS

| | | |
|---|---|---|
| WO | 2005110278 A2 | 11/2005 |
| WO | 2006090372 A3 | 8/2006 |
| WO | 2012097506 A1 | 7/2012 |
| WO | 2014078705 A1 | 5/2014 |
| WO | 2014151939 A1 | 9/2014 |
| WO | 2015138652 A1 | 9/2015 |

OTHER PUBLICATIONS

Adkisson, H.D., et al., "The Potential of Human Allogeneic Juvenile Chondrocytes for Restoration of Articular Cartilage", American Journal of Sports Medicine., vol. 38, No. 7, (Apr. 27, 2010), pp. 1324-1333.

Ahn, et al., "In Vivo Osteogenic Differentiation of Human Adipose-Derived Stem Cells in an Injectable in Situ-Forming D Gel Scaffold", Tissue Eng Part A, (2009), vol. 15, No. 7, pp. 1821-1832.

Albrecht, F., et al. "Closure of Osteochondral Lesions Using Chondral Fragments and Fibrin Adhesive", Archives of Orthopaedic and Traumatic Surgery, vol. 101 (1983): pp. 213-217.

AlloSource. (Sep. 2012). "DeNovo® NT: Natural Tissue Graft", [Brochure]. Centennial, CO. AlloSource. 2 pages.

Angelo, "Micronutrients and Bone Health", Linus Pauling Institute, [accessed on Oct. 20, 2015, retrieved fromthe Internet: <http://lpi.oregonstate.edu/infocenter/bonehealth.html>].

Anghileri, et al., "Neuronal Differentiation Potential of Human Adipose-Derived Mesenchymal Stem Cells", Stem Cells Dev., (2008), vol. 17, No. 5, pp. 909-916.

Arnalich-Montiel, et al., "Adipose-Derived StemCells Are a Source for Cell Therapy of the Corneal Stroma", Stem Cells, (2008), vol. 26, pp. 570-579.

Aubin, et al., "Isolation of Bone Cell Clones with Differences in Growth, Hormone Responses, and Extracellular Matrix Production", 92 J. Cell. Biol. 452-61 (1982).

Baer, et al., "Adipose-Derived Mesenchymal Stromal/Stem Cells: Tissue Localization, Characterization, and Heterogeneity", Stem Cells International, Hidsawi Publishing, vol. 2012, Article ID 812693, 11 pages.

Barry, "Mesenchymal stem cell therapy in joint disease", Tissue engineering of cartilage and bone: Novartis Foundation Symposium, 249, 86-102 (2003).

Bennett, et al., "Adipocytic cells cultured frommarrow have osteogenic potential", J. Cell. Sci. 99, 131-139 (1991).

Brittberg, M., M.D., et al. "Treatment of Deep Cartilage Defects in the Knee with Autologous Chondrocyte Transplantation", The New England Journal of Medicine. vol. 331, No. 14 (Oct. 6, 1994): pp. 889-895.

Bruder, et al., "Tissue Engineering of Bone. Cell Based Strategies", Clin Orthop Relat Res., (1999), vol. 367 Suppl., pp. S68-S83.

Bunnell, et al., "Adipose-Derived Stem Cells: Isolation, Expansion and Differentiation", Methods, (2008), vol. 45, No. 2, pp. 115-120.

Butt, et al., "Stimulation of Peri-Implant Vascularization with Bone Marrow-Derived Progenitor Cells: Monitoring by in Vivo EPR Oximetry", Tissue Eng., (2007), vol. 13, No. 8, pp. 2053-2061.

Cha, et al., "Stem cells in cutaneous wound healing", Clinics in Dermatology 25:73-78 (2007).

Chamberlain, et al., "Concise Review : Mesenchymal Stem Cells: Their Phenotype, Differentiation Capacity, Immunological Features, and Potential for Homing", Stem Cells (2007) 25:2739-2749.

Chen, et al., "Differentiation of Rat Adipose-Derived Stem Cells into Smooth-Muscle-Like Cells in Vitro", Zhonghua Nan Ke Xue, (2009), vol. 15, No. 5, pp. 425-430.

Chen, et al., "Study of MSCs in Vitro Cultured on Demineralized Bone Matrix of Mongrel", Shanghai Kou Qiang Yi Xue, (2007), vol. 16, No. 3, pp. 255-258.

Cheng, et al., "Chondrogenic Differentiation of Adipose-Derived Adult Stem Cells by a Porous Scaffold Derived fromNative Articular Cartilage Extracellular Matrix", Tissue Eng Part A, (2009), vol. 15, No. 2, pp. 231-241.

Chu, et al. "Leukocytes in blood transfusion: adverse effects and their prevention", HKMJ (1999) 5:280-284.

Diekman, et al., "Chondrogenesis of adult stem cells from adipose tissue and bone marrow : Induction by growth factors and cartilage-derived matrix", Tissue Engineering, 16, 523-533 (2010); pub. online Sep. 2009.

Erdmann, J., "ISTO Technologies Aims to Rescue Damaged Joints", Chemistry and Biology, vol. 18, No. 3, (Mar. 1, 2011), pp. 275-276.

Extended European Search Report for European Patent Application No. 13854322.8, mailed on Apr. 25, 2016, all pages.

Extended European Search Report for European Patent Application No. 14754909.1, mailed on Oct. 31, 2016, all pages.

Extended European Search Report for European Patent Application No. 14767334.7, mailed on Oct. 19, 2016, all pages.

Eyre, D., "Collagen of articular cartilage", Arthritis Res. 4:30-35 (2002).

Farr, J., et al. "Chondral defect repair with particulated juvenile cartilage allograft". Electronic Poster. International Cartilage Repair Society, (Sep. 26-29, 2010), Sitges/Barcelona, Spain. Retrieved from <http://posters.webges.com/icrs/epos> on Oct. 11, 2010. 14 pages.

Frisbie, D. D., et al. "In Vivo Evaluation of a One Step Autologous Cartilage Resurfacing Technique in a Long Term Equine Model," Poster #1355. 51st AnnualMeeting of the Orthopaedic Research Society, (May 20-23, 2005), one page.

Gortz, S., et al., "Allografts in Articular Cartilage Repair", The Journal of Bone and Joint Surgery, vol. 88, No. 6, pp. 1374-1384, (Jun. 2006).

Hatic, S.O., et al. "Particulated Juvenile Articular Cartilage Graft (DeNovo NT Graft) for Treatment of OsteochondralLesions of the Talus", Foot and Ankle Specialist, vol. 3, No. 6, (Dec. 1, 2010), pp. 361-361.

International Preliminary Report on Patentability of International Application No. PCT/US2013/070379, mailed on May 28, 2015, all pages.

International Preliminary Report on Patentability of International Application No. PCT/US2014/017816, mailed on Oct. 1, 2015, all pages.

International Preliminary Report on Patentability of International Application No. PCT/US2014/026703, mailed on Sep. 24, 2015, all pages.

International Search Report and Written Opinion of International Application No. PCT/US2013/070379, mailed on Jan. 14, 2014, all pages.

International Search Report and Written Opinion of International Application No. PCT/US2014/017816, mailed on May 19, 2014, all pages.

International Search Report and Written Opinion of International Application No. PCT/US2014/026703, mailed on Jul. 28, 2014, all pages.

Jurgens, Wouter J.F. et al., "Effect of tissue-harvesting site on yield of stem cells derived fromadipose tissue: implications for cell-based therapies", Cell Tissue Res, (2008), 332:415-426.

Knutsen, G., et al., "A Randomized Trial Comparing Autologous Chondrocyte Implantation with Microfracture: Findings at Five Years", The Journal of Bone and Joint Surgery, Inc. vol. 89-A, No. 10, (Oct. 2007), pp. 2105-2112.

Knutsen, G., et al., "Autologous Chondrocyte Implantation Compared with Microfracture in the Knee", The Journal of Bone and Joint Surgery, Inc. vol. 86-A, No. 3, (Mar. 2004), pp. 455-464.

(56) References Cited

OTHER PUBLICATIONS

Lewandrowski, K., et al., "Improved Osteoinduction of Cortical Bone Allografts: A Study of the Effects of Laser Perforation and Partial Demineralization", Journal of Orthopaedic Research, vol. 15, pp. 748-756, (1997).

Lu, Y., et al., "Minced Cartilage without Cell Culture Serves as an Effective Intraoperative Cell Source for Cartilage Repair", Journal of Orthopaedic Research, (Jun. 2006): pp. 1261-1270.

McCulloch, et al., "Osteochondral Allografts for Large Defects in the Knee", Techniques in Knee Surgery, (2006), vol. 5 No. 3, pp. 165-173.

Miller, S., et al., "Fresh Osteochondral Allograft Transplantation-High Chondrocyle Viability 16 Months Posttransplant", Biopreservation and Biobanking, vol. 11, No. 1, pp. 68-69, Feb. 2013.

Mour et al., "Advances in Porous Biomaterials for Dental and Orthopaedic Application", Materials 3(5):2947-2974, (2010).

Outerbridge R.E, et al., "The Biology of Chondromalacia Patellae", J. Bone Joint Surg. Br. 43:752-757, (1961).

Pallante, A., et al., "Chondrocyte Viability is Higher After Prolonged Storage at 37 Than at 4 for Osteochondral Grafts", American Journal Sports Medicine, vol. 37(Suppl. 1), (Nov. 2009). pp. 24S-32S.

Peterson et al., "Osteoinductivity of Commercially Available Demineralized Bone Matrix", The J. of Bone & Joint Surgery, (2004), 8 pages.

Petrochenko et al., "Novel Approaches to Bone Grafting: Porosity, Bone Morphogenetic Proteins, Stem Cells, and the Periosteum," Nat'l Institute of Health Public Access, (2010), 14 pages.

Pietrzak, et al., "Assay of Bone Morphogenetic Protein-2, -4, and -7 in Human Demineralized Bone Matrix", Scientific Foundation, pp. 84-90, (Jun. 1972).

Rhie, J-W., et al., "Chondrogenic differentiation of human adipose-derived stemcells in PLGA (Poly(Lactide-co-Glycolide Acid)) Scaffold", Key Engineering Materials, 342, 345-348, (2007).

Rosa, "Assessment of strategies to increase chondrocyte viability in cryopreserved human osteochondral allografts : evaluation of the glycosylated hydroquinone, arbutin", Osteoarthritis and Cartilage, vol. 17, No. 12, (2009).

Salgado, A.J., et al., "Adult Stem Cells in Bone and Cartilage Tissue Engineering", Current Stem Cell Research & Therapy, (2006), 1:pp. 345-364.

Santos et al., "Multidisciplinary utilization of dimethyl sulfoxide: pharmacological, cellular, and molecular aspects", Biochemical Pharmacology, vol. 65, (2003), pp. 1035-1041.

Sgaglione, "The Future of Cartilage Restoration", The Journal of Knee Surgery, vol. 17, No. 4., pp. 235-243, (Oct. 2004).

Singh, Shikha et al., "Leukocyte depletion for safe blood transfusion", Biotechnol J, (2009), 4:1140-1151.

Stone, K. R., et al. "Articular Cartilage Paste Grafting to Full-Thickness Articular Cartilage Knee Joint Lesions: A 2- to 12-Year Follow-up", Arthroscopy: The Journal of Arthroscopc and Related Surgery, vol. 22, No. 3, (Mar. 2006), pp. 291-299.

Strong, et al. "Freeze-Drying of Tissues", Musculoskeletal Tissue Banking, (1993), (WWWTomford ed.) Ravens Press, NY, 28 pages.

Trice, M., "American Academy of Orthopaedic Surgeons 77th Annual Meeting Mar. 9-13, 2010 New Orleans, Louisiana Committee on Biological Implants Articular Cartilage Restoration: A Review of Currently Available Methods", (Jan. 1, 2010), <http://www.aaos.org/research/committee/biologic/BI_SE_2010.pdf>.

Wan, et al., "Biphasic scaffold for annulus fibrosus tissue regeneration", Biomaterials, vol. 29, pp. 643-652, (2008).

Whiteside, et al., "Impact loading of articular cartilage during transplantation of osteochondral autograft", The Journal of Bone & Joint Surgery, vol. 87-B, No. 9, (Sep. 2005), pp. 1285-1291.

Yang, Q. et al., "A cartilage ECM-derived 3-D porous acellular matrix scaffold for in vivo cartilage tissue engineering with PKH26-labeled chondrogenic bone marrow-derived mesenchymal stemcells", Biomaterials, 29, 2378-2387, (2008).

Yoon, et al., "In Vivo Osteogenic Potential of Human Adipose-Derived Stem Cells/Poly Lactide-Co-Glycolic Acid Constructs for Bone Regeneration in a Rat Critical-Sized Calvarial Defect Model", Tissue Eng., (2007), vol. 13, No. 3, pp. 619-627.

Zimmer, "Articular Cartilage Repair: Basic Science", Zimmer Technical Memo, (2009) Zimmer, Inc., 3 pages.

Zimmer, Inc., "Biologic treatment for early intervention and cartilage repair" NT Natural Tissue Graft Surgical Technique, (Jan. 1, 2009), Retrieved fromthe internet: <http://www.zimmer.com/content/dam/zimmer-web/documents/en-US/pdf/surgical-techniques/knee/zimmer-denovo-nt-natural-tissue-graft-surgical-technique.pdf>.

* cited by examiner

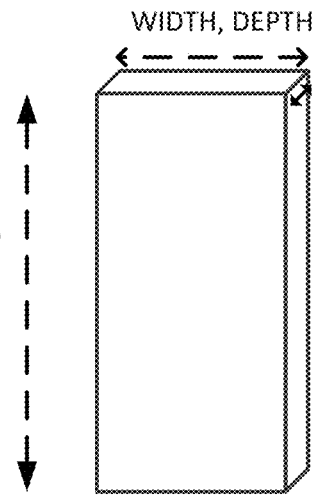
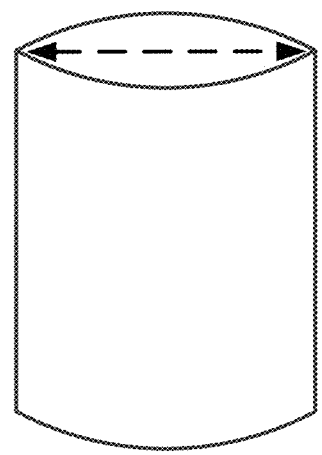
FIG. 1A
FIG. 1B
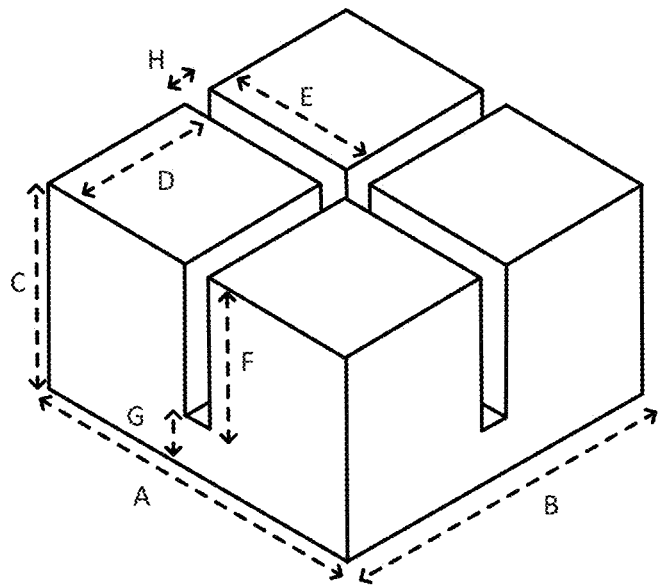
FIG. 1C
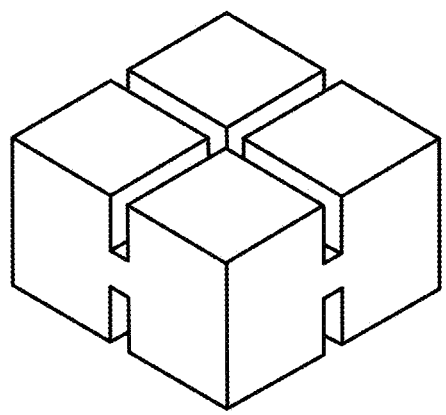
FIG. 1D

ADULT DONOR A (fluorescence readings)

JUVENILE DONOR B (fluorescence readings)

|  | | Day 1 cell # 0.3cc | 6wk cell# .3cc explant | Cell outgrowth |
|---|---|---|---|---|
| Adult-124594 | Laser | 66490 | 956052 | 889562 |
|  | Hand cut | 266033 | 987022 | 720989 |
| Juvenile-124953 | Laser | 772345 | 1012770 | 240425 |
|  | Hand cut | 803742 | 1143297 | 339555 |

FIG. 4

(Donor C, D, E, F, and G)

| Donor # | Laser Cut | Hand Cut | De novo | Laser Cut | Hand Cut |
|---|---|---|---|---|---|
| 1 | 390,000 | 360,000 | 4,176,788 | 85% | 91% |
| 2 | 1,433,333 | 176,666 | 813,570.4 | 88% | 71% |
| 3 | 295,000 | 237,500 | 1,452,609 | 85% | 92% |
| 4 | 2,625,000 | 890,000 | | 90% | 87% |
| 5 | 517,500 | 212,500 | | 83% | 89% |
| | 1,052,167 | 375,333 | 2,147,656 | 86% | 86% |
| | 989,536 | 295,846 | 1,786,092 | 3% | 9% |

| | Laser Cut | Hand Cut | De novo | Laser Cut | Hand Cut | |
|---|---|---|---|---|---|---|
| Tryphan Blue | 1,052,167 | 375,333 | | | | |
| Presto Blue | 2,607,441 | 2,672,802 | 2,147,656 | 86% | 86% | AVG |
| STDEV | 989,536 | 295,846 | 1,786,092 | 3% | 9% | STDEV |
| | 1,108,534 | 1,397,028 | | | | |

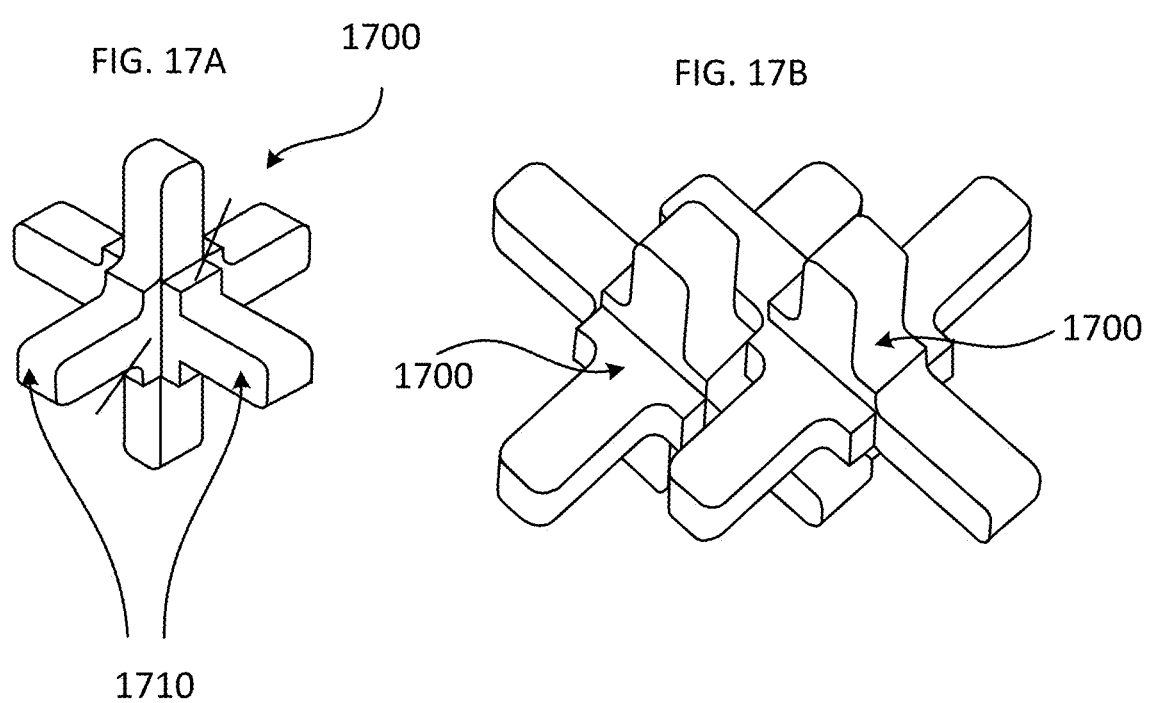

CARTILAGE MOSAIC COMPOSITIONS AND METHODS

CROSS-REFERENCES TO RELATED APPLICATIONS

This application is a continuation application of U.S. patent application Ser. No. 16/459,136, filed Jul. 1, 2019, which is a continuation application of U.S. patent application Ser. No. 15/608,679, filed May 30, 2017, which is a continuation application of U.S. patent application Ser. No. 14/875,258, filed Oct. 5, 2015, now U.S. Pat. No. 9,700,415, issued Jul. 11, 2017, which is a continuation application of U.S. patent application Ser. No. 14/187,093, filed Feb. 21, 2014, now U.S. Pat. No. 9,186,253, issued Nov. 17, 2015, which claims the benefit of priority of U.S. Provisional Patent Application No. 61/768,190, filed Feb. 22, 2013, the entire contents of each of which are incorporated herein by reference.

BACKGROUND

Cartilage tissue can be found throughout the human anatomy. The cells within cartilage tissue are called chondrocytes. These cells generate proteins, such as collagen, proteoglycan, and elastin, that are involved in the formation and maintenance of the cartilage. Hyaline cartilage is present on certain bone surfaces, where it is commonly referred to as articular cartilage. Articular cartilage contains significant amounts of collagen (about two-thirds of the dry weight of articular cartilage), and cross-linking of the collagen imparts a high material strength and firmness to the tissue. These mechanical properties are important to the proper performance of the articular cartilage within the body.

Articular cartilage is not vascularized, and when damaged as a result of trauma or degenerative causes, this tissue has little or no capacity for in vivo self-repair. A variety of therapeutic solutions have been proposed for the treatment and repair of damaged or degenerated cartilage. Tissue healing involves cell migration that redistributes cells from the surrounding tissues to the injury site. In cartilage tissue, however, the ability of chondrocytes to migrate from their native lacunae site may be very limited due to the supposed rigidity of the matrix. To compensate for the migration deficiency, various surgical interventions for cartilage repair focus on delivering reparative cells or tissues. For example, marrow stimulation attempts to tap marrow cells by breaching the subchondral bone, although the mechanical durability of resultant fibrocartilage is often unsatisfactory. Autologous chondrocyte implantation (ACI) directly establishes a chondrocyte presence in the treatment site through the delivery of culture-expanded chondrocytes. Despite being associated with some measure of clinical success, ACI is associated with technical hurdles such as the cell culture preparation, two-stage surgical procedure, and challenging procedural aspects to place small pieces of cartilage into the defect sites.

BRIEF SUMMARY

In one aspect, mosaic cartilage compositions are provided. In some embodiments, the composition comprises:
  a cartilage sheet comprising a plurality of interconnected cartilage tiles; and
  a biocompatible carrier.

In some embodiments, the composition comprises tiles that are separated by channels having a depth that is less than the maximum thickness of the cartilage sheet. In some embodiments, the cartilage sheet has a maximum thickness of about 0.25 mm to about 5 mm. In some embodiments, the cartilage that is beneath the channels has a thickness of less than 0.25 mm.

In some embodiments, the composition comprises tiles that are separated by perforations. In some embodiments, the perforations are microperforations.

In some embodiments, the cartilage is articular cartilage. In some embodiments, the cartilage is non-decellularized cartilage. In some embodiments, the cartilage is from a human adult cadaveric donor age 15 years or older. In some embodiments, the cartilage is from a human juvenile cadaveric donor.

In some embodiments, the tiles are circular in shape. In some embodiments, the tiles have an average diameter from about 0.5 mm to about 3 mm. In some embodiments, the tiles are square or rectangular in shape. In some embodiments, the cartilage tiles have an average length and/or width from about 0.5 mm to about 3 mm. In some embodiments, the tiles are substantially uniform in size and/or shape.

In some embodiments, the cartilage sheet further comprises perforations in the cartilage beneath one or more channels. In some embodiments, the perforations are microperforations.

In some embodiments, the biocompatible carrier comprises a cryopreservation medium. In some embodiments, the cryopreservation medium comprises dimethyl sulfoxide (DMSO) and serum.

In some embodiments, at least a portion of the cartilage sheet is coated with a biological adhesive. In some embodiments, the biological adhesive is fibrin, fibrinogen, thrombin, fibrin glue, polysaccharide gel, cyanoacrylate glue, gelatin-resorcin-formalin adhesive, collagen gel, synthetic acrylate-based adhesive, cellulose-based adhesive, basement membrane matrix, laminin, elastin, proteoglycans, autologous glue, or a combination thereof.

In some embodiments, at least a portion of the cartilage sheet is combined with demineralized bone. In some embodiments, at least a portion of the cartilage sheet is combined with a bone or cartilage substrate that is seeded with stem cells.

In another aspect, methods of manufacturing a mosaic cartilage composition are provided. In some embodiments, the method comprises:
  obtaining cartilage tissue from a human cadaveric donor;
  cutting a plurality of channels or perforations into the cartilage tissue, thereby forming a cartilage sheet comprising a plurality of interconnected cartilage tiles that are separated by the channels; and
  suspending the cartilage sheet in a biocompatible medium.

In some embodiments, the cutting step comprises cutting a plurality of channels into the cartilage tissue, wherein each of the plurality of channels has a depth that is less than the maximum thickness of the cartilage tissue. In some embodiments, prior to the cutting step, the cartilage tissue has a maximum thickness of about 0.25 mm to about 5 mm. In some embodiments, the cartilage that is beneath the plurality of channels has a thickness of less than 0.25 mm.

In some embodiments, the cutting step comprises cutting a plurality of perforations into the cartilage. In some embodiments, the perforations are microperforations.

In some embodiments, the cartilage tissue is articular cartilage tissue. In some embodiments, the cartilage tissue is from a human adult cadaveric donor age 15 years or older. In some embodiments, the cartilage tissue is from a human juvenile cadaveric donor.

In some embodiments, the cutting step comprises cutting the cartilage tissue with a laser cutter, with a mechanical blade, or with a mechanical press. In some embodiments, the cutting step comprises cutting the cartilage tissue with a laser cutter. In some embodiments, the cutting step comprising cutting the cartilage tissue with the laser cutter at a speed from about 15% to about 55%, a power from about 2% to about 65%, and a frequency from about 200 Hz to about 2600 Hz.

In some embodiments, the cutting step comprises forming tiles that are circular in shape. In some embodiments, the tiles have an average diameter from about 0.5 mm to about 3 mm. In some embodiments, the cutting step comprises forming tiles that are square or rectangular in shape. In some embodiments, the tiles have an average length and/or width from about 0.5 mm to about 3 mm. In some embodiments, the cutting step comprises forming tiles that are substantially uniform in size and/or shape.

In some embodiments, the method further comprises making perforations in cartilage beneath one or more of the channels. In some embodiments, the perforations are microperforations.

In some embodiments, following the cutting step, the method further comprises washing the cartilage sheet with a saline solution.

In some embodiments, the biocompatible carrier comprises a cryopreservation medium. In some embodiments, the cryopreservation medium comprises dimethyl sulfoxide (DMSO) and serum.

In some embodiments, prior to the suspending step, the method further comprises coating at least a portion of the cartilage sheet with a biological adhesive. In some embodiments, prior to the suspending step, the method further comprises combining at least a portion of the cartilage sheet with demineralized bone. In some embodiments, prior to the suspending step, the method further comprises combining at least a portion of the cartilage sheet with a bone or cartilage substrate seeded with stem cells.

In another aspect, methods of treating a cartilage or bone defect in a subject are provided. In some embodiments, the method comprises administering to the subject a mosaic cartilage composition as described herein.

In yet another aspect, methods of repairing cartilage in a subject are provided. In some embodiments, the method comprises administering to the subject a mosaic cartilage composition as described herein.

In still another aspect, kits (e.g., for treating a cartilage or bone defect in a subject or for repairing cartilage in a subject) are provided. In some embodiments, the kit comprises a mosaic cartilage composition as described herein.

BRIEF DESCRIPTION OF THE DRAWINGS

FIGS. 1A-1D. Examples of cartilage constructs processed from cartilage tissue. FIG. 1A shows that cartilage can be cut into particles having a rectangular columnar shape. FIG. 1B shows that cartilage particles can be cut into particles having a cylindrical or elliptical columnar shape. FIG. 1C shows that cartilage can be cut into interconnected tiled or mosaic constructs. For example, the cartilage construct can have a width A, length B, and height C. Cuts, etches, or channels in the construct have a depth F and width H. Individual columns have a height F, width E, and length D. Subsequent to cutting, the construct has a minimum thickness G. FIG. 1D shows that a cartilage tissue can be cut, for example using a laser, on two or more sides (e.g., top and bottom).

FIG. 4. Mean fluorescence readings for chondrocyte samples from an adult donor and from a juvenile donor, measured at day 1 and after culturing for 6 weeks.

FIG. 5. Trypan Blue cell viability assay for Donors C, D, E, F, and G (also referred to as donors 1, 2, 3, 4, and 5, respectively). Cell viability was determined for laser cut and hand cut cartilage particles. The average cell viability is presented as a percentage. The term "Denovo" refers to a juvenile cartilage product that is hand cut into 1 mm squares.

FIG. 11A shows an exemplary mosaic cartilage construct. The mosaic cartilage construct 1100 can include multiple tiles that are separated by channels of a desired width or dimension. The tiles may be of any desired shape (e.g., squares) and may have any desired dimension (e.g., about 1 mm×1 mm square). The mosaic cartilage construct can also include one or more apertures 1110. For example, apertures 1110 may represent holes or passages that extend through the construct, from one side of the construct (e.g., a top surface) to an opposing side of the construct (e.g., a bottom surface). Apertures 1110 can be of any desired shape (e.g., square, circle, or oval), and may have any desired dimension (e.g., about 1 mm diameter circle, about 1 mm×1 mm square). As shown in FIG. 11B, apertures in the mosaic cartilage construct can operate to allow or enhance nutrient or liquid perfusion within and throughout the mosaic cartilage construct.

FIGS. 17A-17B. A cartilage particle having interlocking shapes is shown in FIG. 17A. The cartilage particle 1700 has multiple projections 1710. As shown in FIG. 17B, the projections of the cartilage particle can interlock with the projections of a second cartilage particle having multiple projections, thus operating to keep the particles together, or to inhibit the particles from moving relative to one another, for example after being applied to a treatment site.

DETAILED DESCRIPTION

I. Introduction

Figure 2:
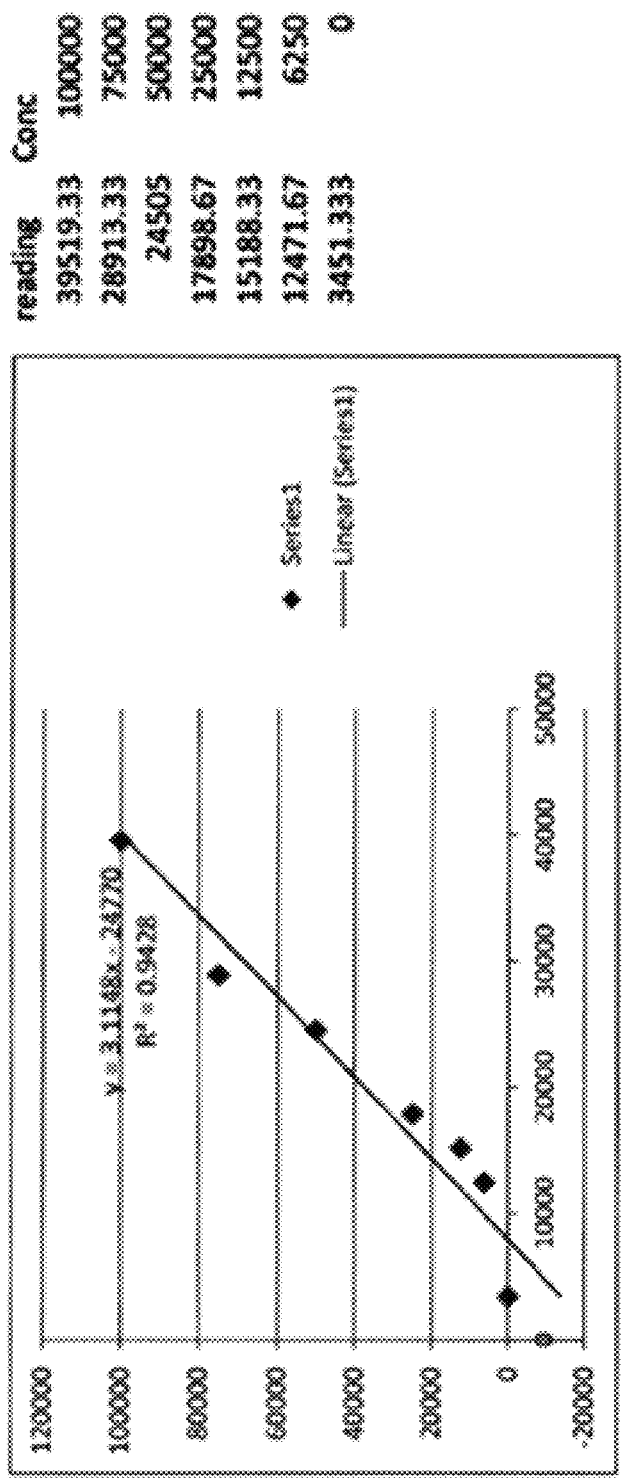
FIG. 2. A standard curve for samples having known concentrations of chondrocytes. The y-axis represents fluorescence readings from a Countess® automated cell counter, and the x-axis represents the chondrocyte concentration (cells/μl).

In one aspect, the present invention relates to mosaic cartilage constructs comprising multiple interconnected cartilage tiles for cartilage and/or bone repair and regeneration. The mosaic cartilage constructs disclosed herein provide a large surface area for facilitating or promoting chondrocyte outgrowth from the cartilage construct into an application site (e.g., a site of bone or cartilage injury), while the interconnectedness of the multiple tiles in the construct also promotes easier handling or surgical implantation as compared to traditional autologous chondrocyte implantation (ACI) or mosaicplasty. Additionally, perforations in the cartilage facilitate the transfusion of nutrients within, throughout, and across the cartilage construct, thereby enhancing chondrocyte outgrowth from the cartilage construct.

II. Definitions

As used herein, the term "interconnected tiles," as used with reference to a cartilage construct or sheet comprising multiple cartilage tiles, refers to cartilage tiles that are partially or incompletely connected, via cartilage tissue, to one or more other cartilage tiles within the sheet. As a non-limiting example, a sheet of cartilage into which perforated lines have been cut, wherein the perforated lines separate the cartilage into multiple smaller portions, or tiles, comprises cartilage tiles that are "partially connected." In contrast, an uncut sheet of cartilage (e.g., a sheet of cartilage that has not been perforated) is "completely connected." In some embodiments, interconnected cartilage tiles are separated by discontinuous perforations (e.g., microperforations, apertures, bores, holes, or other passages), and a cartilage tile remains partially connected to one or more other cartilage tiles via non-perforated cartilage adjacent to the perforated cartilage. In some embodiments, interconnected cartilage tiles are separated by channels that have a depth less than that of the depth of the cartilage tiles, and a cartilage tile remains partially connected to one or more other cartilage tiles via the cartilage beneath the channels. In some embodiments, the interconnected cartilage tiles are all cut from a single piece of cartilage.

As used herein, the term "human adult donor" refers to a human donor that is 15 years of age or older. In some embodiments, a human adult donor is at least 18 years of age or older at the time of donation.

As used herein, the term "human juvenile donor" refers to a human donor that is 12 years of age or younger. In some embodiments, a human juvenile donor is between the ages of 1 and 12 at the time of donation.

III. Cartilage Compositions

In one aspect, mosaic cartilage constructs are provided. In some embodiments, the composition comprises: a cartilage sheet comprising a plurality of interconnected tiles, wherein the tiles are separated by channels having a depth that is less than the maximum thickness of the cartilage sheet; and a biocompatible carrier. In some embodiments, the cartilage sheet comprises a plurality of interconnected tiles are separated by perforations. In some embodiments, the cartilage sheet comprises a plurality of interconnected tiles are separated by channels, wherein the channels have a depth that is less than the maximum thickness of the cartilage sheet (e.g., less than the thickness of the tiles).

Cartilage Tile Formation and Separation

In some embodiments, the mosaic cartilage composition comprises a cartilage sheet that has been cut into a plurality of interconnected tiles. The interconnected cartilage tiles can be shaped as circles, squares, rectangles, triangles, ovals, polygons, zig-zags, irregular shapes, and the like, or other desired shape or combination of shapes. In some embodiments, the tiles are substantially uniform in size and/or shape. In some embodiments, the cartilage sheet comprises tile having different sizes and/or shapes. The interconnected tiles in the mosaic pattern hold together as a single unit, and also can operate to interconnect or engage with tiles on other cartilage constructs which may also be applied to a treatment site.

Figure 12:
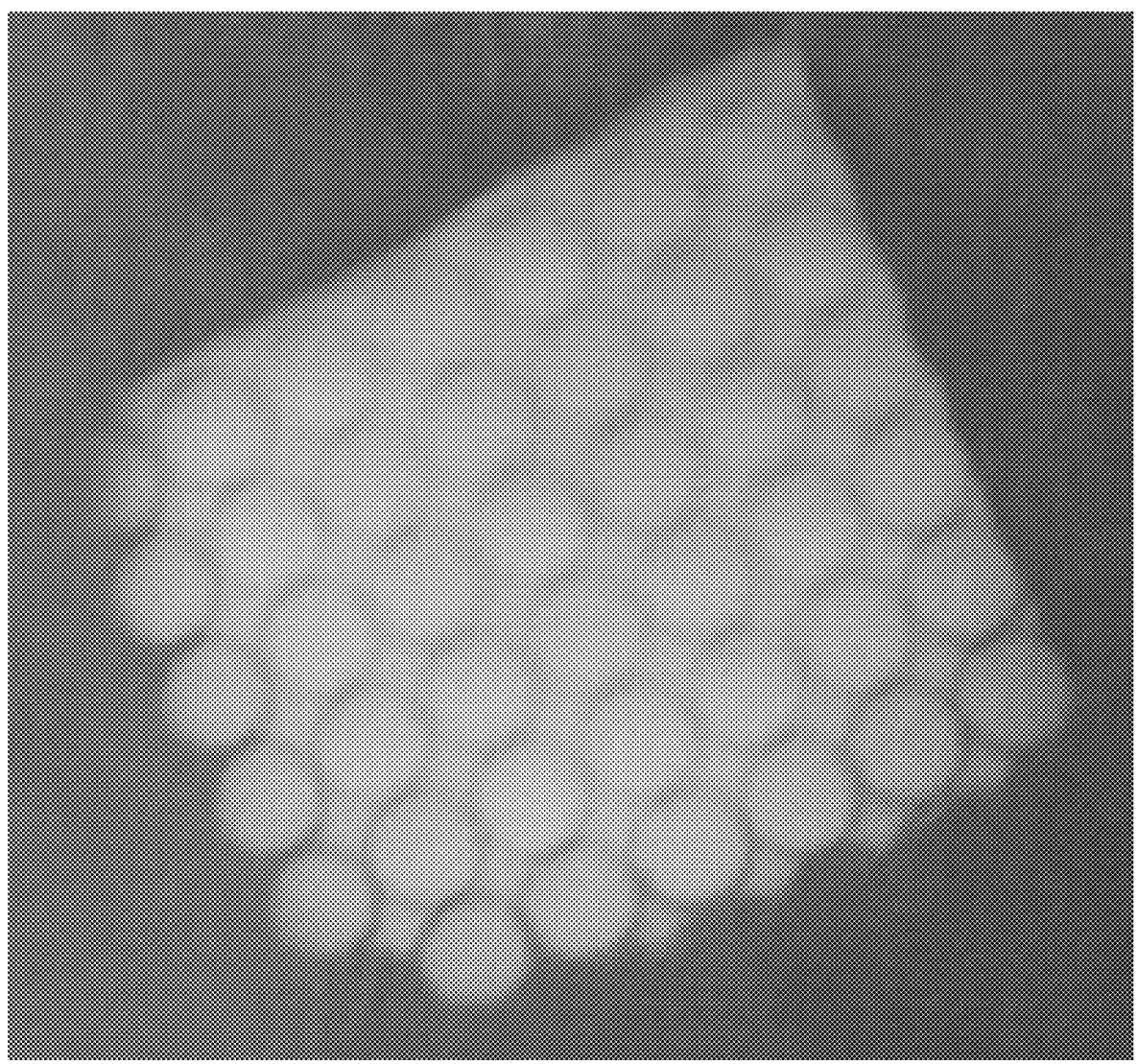
FIG. 12. An exemplary mosaic cartilage construct 1200 comprising a mosaic pattern or circle-shaped tiles.
Figure 13:
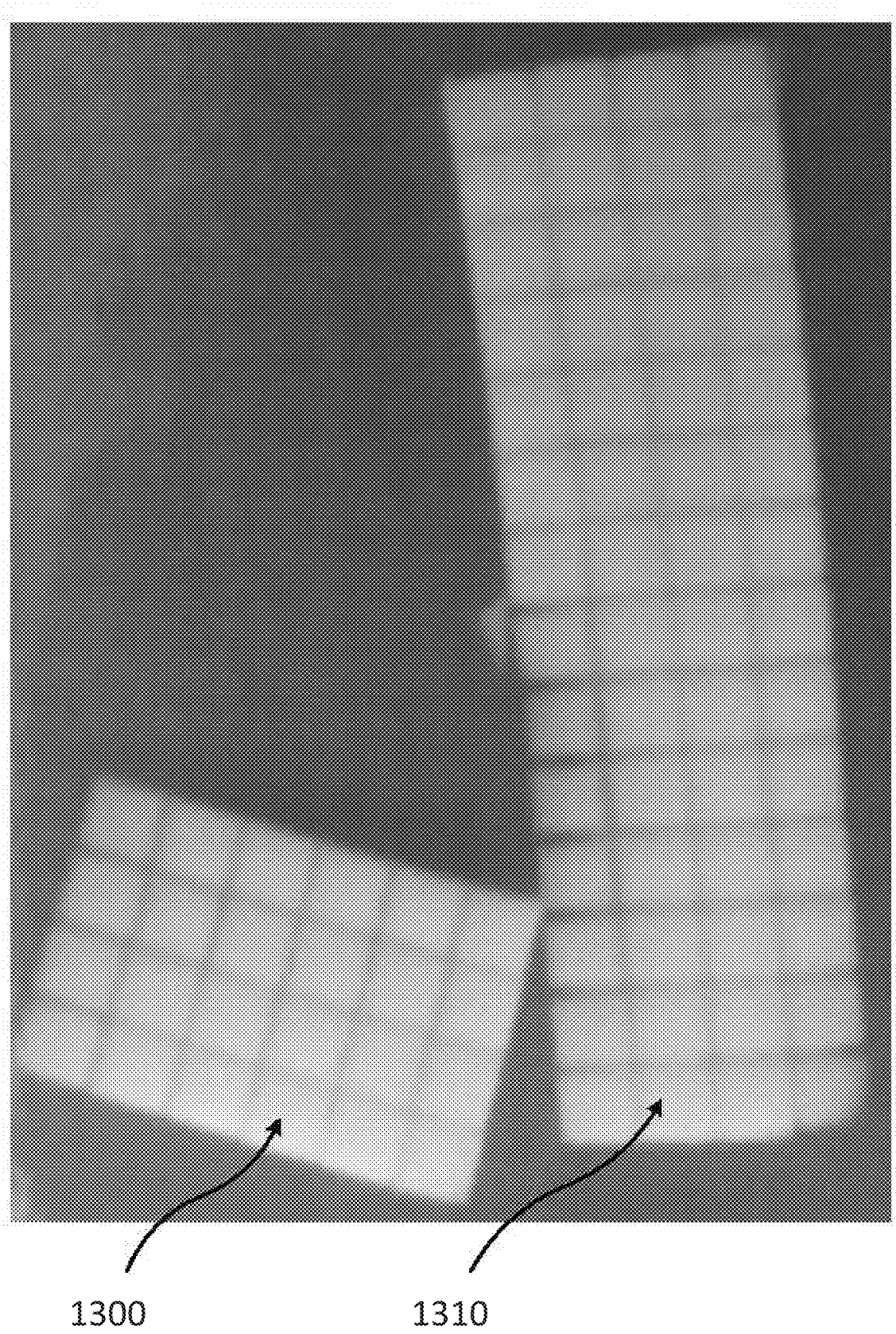
FIG. 13. Two exemplary mosaic cartilage constructs 1300 and 1310, each comprising a mosaic pattern of square-shaped tiles.

In some embodiments, the mosaic cartilage construct comprises a cartilage sheet of interconnected tiles having a circular shape. FIG. 12 shows an exemplary cartilage construct 1200 having a circle mosaic pattern, wherein the circle-shaped tiles are separated by perforations. In some embodiments, the mosaic cartilage construct comprises a cartilage sheet of interconnected tiles having a square and/or rectangular shape. FIG. 13 shows two exemplary cartilage constructs 1300 each having a square mosaic pattern, wherein the square-shaped tiles are separated by perforations.

In some embodiments, the cartilage sheet has a thickness of about 0.25 mm to about 5 mm (e.g., about 0.25 mm, about 0.5 mm, about 0.75 mm, about 1 mm, about 1.5 mm, about 2 mm, about 2.5 mm, about 3 mm, about 3.5 mm, about 4 mm, about 4.5 mm, or about 5 mm). In some embodiments, the cartilage sheet has a "maximum thickness," e.g., the thickness of the cartilage tiles, and a "minimum thickness," e.g., the thickness of cartilage beneath one or more channels separating the cartilage tiles. In some embodiments, the cartilage sheet has a maximum thickness of about 0.25 mm to about 5 mm (e.g., about 0.25 mm, about 0.5 mm, about 0.75 mm, about 1 mm, about 1.5 mm, about 2 mm, about 2.5 mm, about 3 mm, about 3.5 mm, about 4 mm, about 4.5 mm, or about 5 mm). In some embodiments, the cartilage sheet has a minimum thickness of less than about 0.25 mm, e.g., less than about 0.2 mm, about 0.15 mm, about 0.1 mm, about 0.09 mm, about 0.08 mm, about 0.07 mm, about 0.06 mm, about 0.05 mm, about 0.04 mm, about 0.03 mm, about 0.02 mm, or about 0.01 mm.

In some embodiments, the cartilage tiles have an average length and/or an average width from about 0.5 mm to about 3 mm (e.g., about 0.5 mm, about 0.6 mm, about 0.7 mm, about 0.8 mm, about 0.9 mm, about 1 mm, about 1.5 mm, about 2 mm, about 2.5 mm, or about 3 mm). In some embodiments, the cartilage tiles have an average diameter from about 0.5 mm to about 3 mm (e.g., about 0.5 mm, about 0.6 mm, about 0.7 mm, about 0.8 mm, about 0.9 mm, about 1 mm, about 1.5 mm, about 2 mm, about 2.5 mm, or about 3 mm).

In some embodiments, the cartilage sheet has a length and/or a width of about 4 mm, about 5 mm, about 6 mm, about 7 mm, about 8 mm, about 9 mm, about 10 mm, about 15 mm, about 20 mm, about 25 mm, about 30 mm, about 35 mm, about 40 mm, about 45 mm, about 50 mm, about 60 mm, about 70 mm, about 80 mm, about 90 mm, or about 100 mm. In some embodiments, the cartilage sheet has a diameter of about 4 mm, about 5 mm, about 6 mm, about 7 mm, about 8 mm, about 9 mm, about 10 mm, about 15 mm, about 20 mm, about 25 mm, about 30 mm, about 35 mm, about 40 mm, about 45 mm, about 50 mm, about 60 mm, about 70 mm, about 80 mm, about 90 mm, or about 100 mm.

Figure 18:
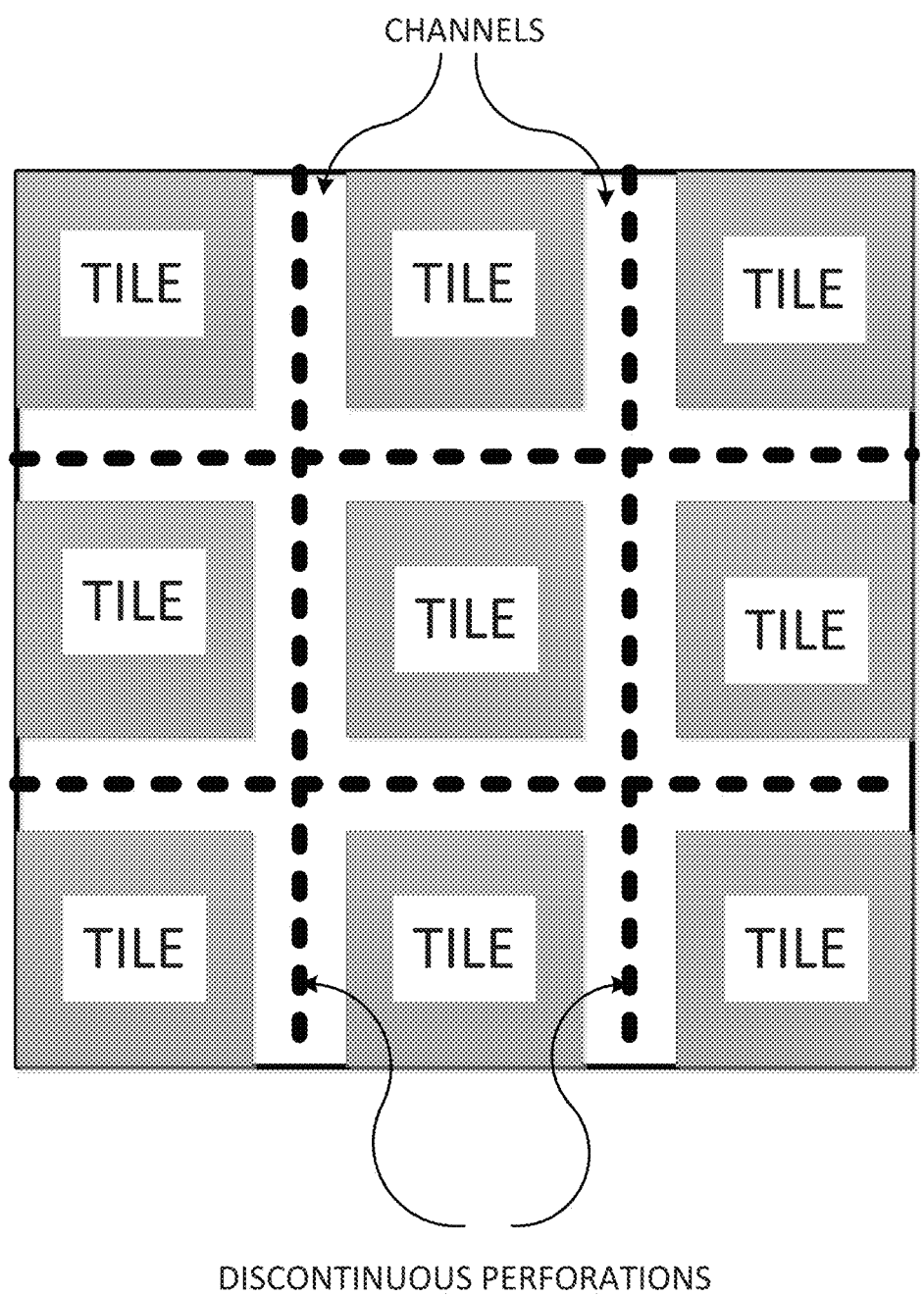
FIG. 18. A cartilage construct having multiple tiles separated by intervening channel sections. Discontinuous perforations can also be applied to the channels (e.g., forming a dotted line down the channels so as to provide a tear strip or perforated tear line feature). Thus, a cartilage construct can include both channel sections and perforations in the channel sections. Such perforations, which can extend through the thickness of the cartilage construct, can allow the migration of nutrients and cells from an underlying bone or tissue to which the cartilage construct is applied.
Figure 19:
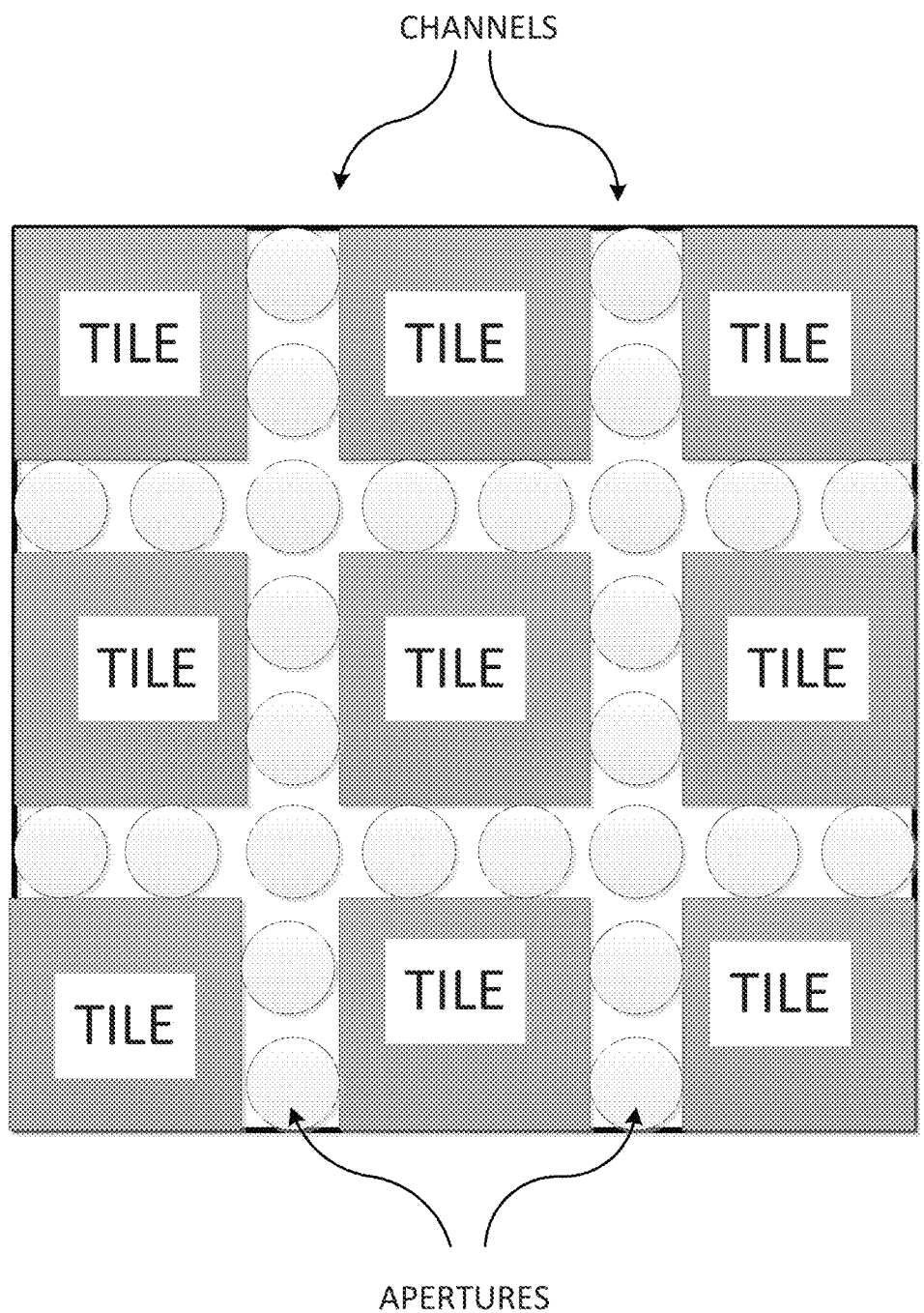
FIG. 19. A cartilage construct having multiple tiles separated by intervening channel sections. Discontinuous apertures can be applied to the channels (e.g., forming a dotted line down the channels). The open aperture ratio can be varied. For the construct depicted in FIG. 19, the open aperture ratio is larger than that of the perforations shown in FIG. 18.
Figure 24:
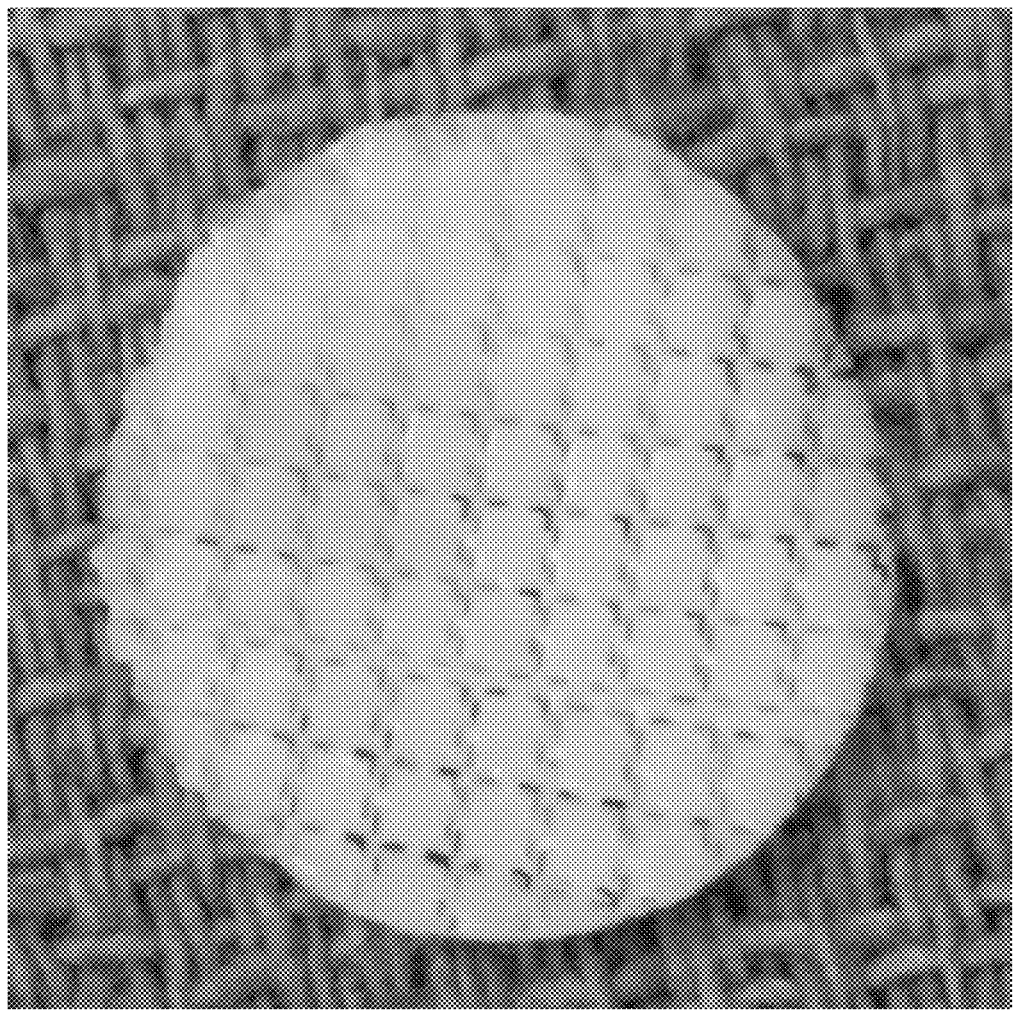
FIG. 24. Perforated mosaic cartilage composition produced by laser cutting.

In some embodiments, the interconnected tiles are separated by perforations (e.g., microperforations, bores, apertures, and the like). An example of a mosaic cartilage composition comprising interconnected tiles separated by perforations is shown in FIG. 24. In some embodiments, the perforations have an average diameter of about 5 microns, about 10 microns, about 15 microns, about 20 microns, about 25 microns, about 30 microns, about 35 microns, about 40 microns, about 45 microns, about 50 microns, about 60 microns, about 70 microns, about 80 microns, about 90 microns, or about 100 microns. Accordingly, in some embodiments, cartilage constructs are provided that have a porous characteristic. In some embodiments, the total cross-sectional area of the perforations (e.g., apertures) can be relatively small in comparison to the total cross-sectional area of the cartilage construct itself. In some embodiments, the aperture area ratio can be higher. Hence open aperture ratios can vary as desired. In some embodiments, the open aperture ratio can be within a range of 0% to 50% or higher. Constructs with greater open aperture ratios may operate to enhance the flow of nutrients at the treatment site. In some embodiments, the open aperture ratio is zero or substantially zero, such that the construct forms a continuous or substantially continuous sheet See, e.g., FIG. 18 and FIG. 19. The open aperture ratio depicted in FIG. 19 is larger than that shown in FIG. 18.

In some embodiments, the interconnected tiles are separated by channels, wherein the channels have a depth that is less than the maximum thickness of the cartilage sheet (e.g., less than the thickness of the tiles). In some embodiments, the channels have a depth of about 0.2 mm, about 0.3 mm, about 0.4 mm, about 0.5 mm, about 0.6 mm, about 0.7 mm, about 0.8 mm, about 0.9 mm, about 1 mm, about 1.5 mm, about 2 mm, about 2.5 mm, about 3 mm, about 3.5 mm, or about 4 mm. In some embodiments, wherein the cartilage sheet comprises channels separating the tiles, the cartilage sheet further comprises perforations in the cartilage beneath one or more of the channels.

In some embodiments, the channels or perforations (e.g., microperforated) sections can present score features, such that a user (e.g., a physician or surgeon) can easily separate or break the cartilage construct into two or more pieces.

Cartilage Source

In some embodiments, the cartilage is articular cartilage. In some embodiments, the articular cartilage is obtained from an articular surface of a joint (e.g., a knee joint or an elbow joint) or from a long bone (e.g., femur or tibia).

In some embodiments, the cartilage is from a human adult cadaveric donor. In some embodiments, the donor is an adult cadaveric donor that is 18 years of age or older at the time of the donation. In some embodiments, the donor is an adult cadaveric donor that is between the ages of 15 and 45 at the time of the donation. In some embodiments, the cartilage is from a human juvenile cadaveric donor. In some embodiments, the donor is a juvenile cadaveric donor that is between the ages of 3 and 12 at the time of the donation.

Biocompatible Carrier

In some embodiments, the biocompatible carrier comprises a buffered solution. In some embodiments, the biocompatible carrier comprises a cryopreservation medium. In some embodiments, the cryopreservation medium comprises dimethyl sulfoxide (DMSO) and serum. In some embodiments, the biocompatible carrier comprises one or more cryoprotective agents such as, but not limited to, glycerol, DMSO, hydroxyethyl starch, polyethylene glycol, propanediol, ethylene glycol, butanediol, polyvinylpyrrolidone, or alginate.

In some embodiments, the biocompatible carrier comprises a growth medium. Suitable examples of growth medium include, but are not limited to, Dulbecco's Modified Eagle's Medium (DMEM) with 5% Fetal Bovine Serum (FBS). In some embodiments, growth medium includes a high glucose DMEM. In some embodiments, the biocompatible carrier (e.g., growth medium) comprises one or more antibiotics.

Additional Biological Components

Figure 14:
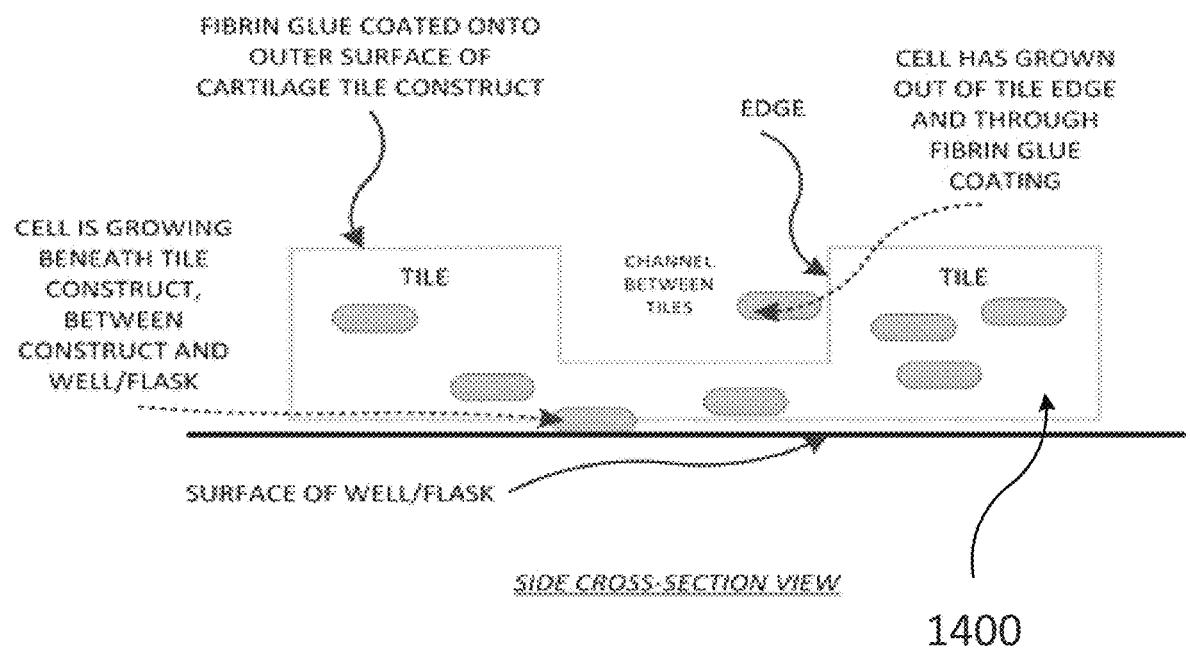
FIG. 14. A mosaic cartilage construct 1400 can be coated with a biological adhesive (e.g., fibrin gel or glue material), which can be used to secure the construct to a culture flask or well or to an application site. Cells can grow out of the cartilage construct, for example out of a tile and into a channel disposed between two tiles. Similarly, cells can grow out of other construct surfaces, for example between the cartilage and an application site (e.g., the surface of a flask, plate well, or patient treatment site).
Figure 15:
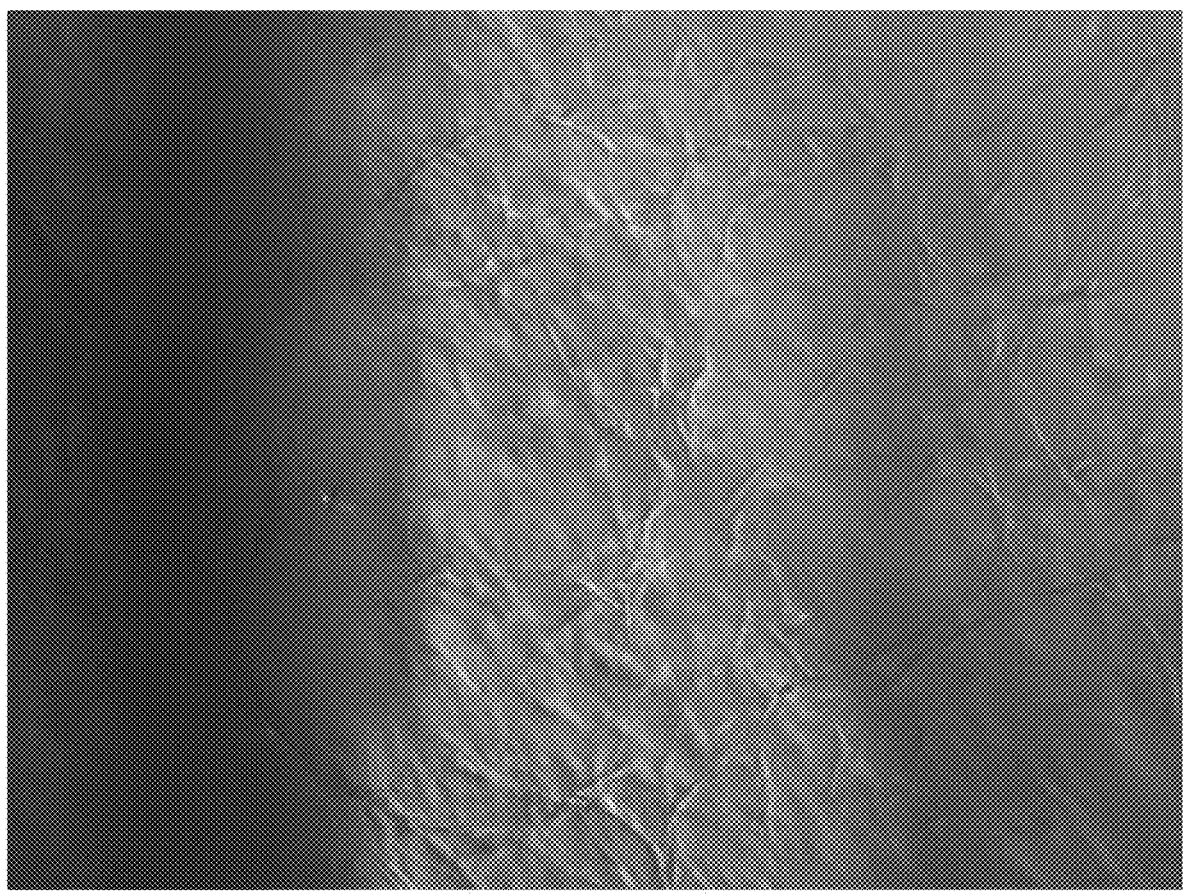
FIG. 15. A juvenile mosaic cartilage construct at day 13, 10× magnification. Cells can be seen growing out of the mosaic cartilage edge and underneath the cartilage construct.
Figure 16A:
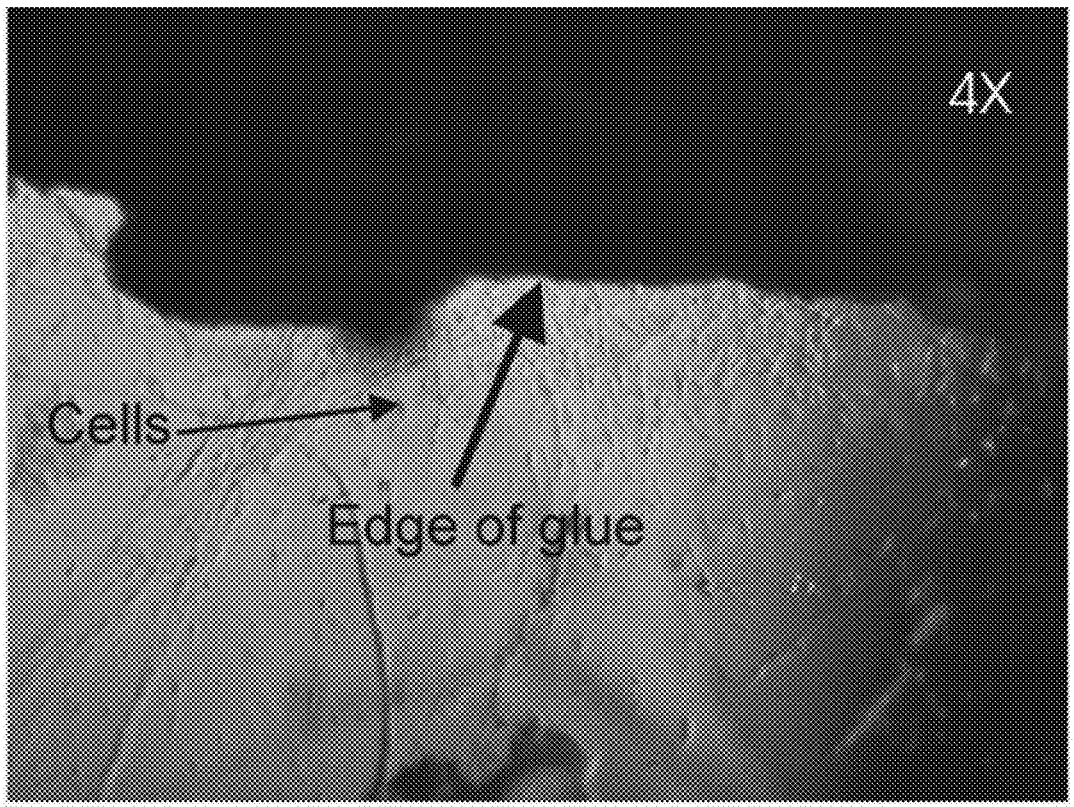
FIGS. 16A-16B. A 4× magnification and 10× magnification of a mosaic cartilage construct are shown in FIG. 16A and FIG. 16B, respectively. In both images, cartilage cells can be seen growing out of the cartilage construct, through the fibrin glue, and away from the construct.
Figure 16B:
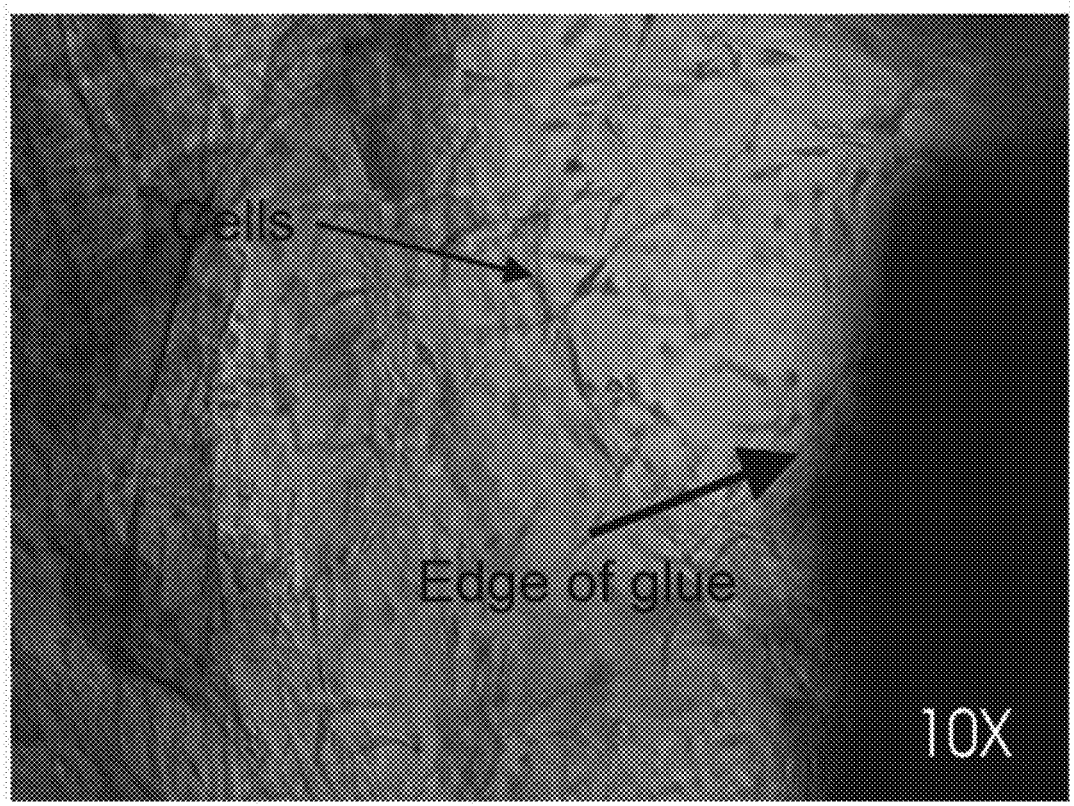

In some embodiments, the mosaic cartilage composition is combined one or more other biological components. For example, in some embodiments, at least a portion of the mosaic cartilage composition is coated with a biological adhesive. See, e.g., FIG. 14. Suitable biological adhesives include, but are not limited to, fibrin, fibrinogen, thrombin, fibrin glue (e.g., TISSEEL), polysaccharide gel, cyanoacrylate glue, gelatin-resorcin-formalin adhesive, collagen gel, synthetic acrylate-based adhesive, cellulose-based adhesive, basement membrane matrix (e.g., MATRIGEL®, BD Biosciences, San Jose, CA), laminin, elastin, proteoglycans, autologous glue, and combinations thereof.

In some embodiments, the mosaic cartilage composition is combined with demineralized bone matrix. For example, in some embodiments the mosaic cartilage composition is combined with demineralized bone matrix at a ratio of about 4:1, about 3:1, about 2:1, or about 1:1 demineralized bone matrix: mosaic cartilage. Demineralized bone matrix can be prepared, e.g., by subjecting a bone substrate to acid, e.g., hydrochloric acid (HCl). Demineralized bone matrix is also commercially available.

In some embodiments, the mosaic cartilage composition is combined with cells such as stem cells. In some embodiments, the mosaic cartilage composition is combined with a bone or cartilage substrate that is seeded with stem cells. For example, in some embodiments, the mosaic cartilage composition is combined with a bone or cartilage substrate (e.g., cortical and/or cancellous bone substrate, demineralized cortical and/or cancellous bone substrate, an osteochondral substrate, or a cartilage substrate) that is seeded with mesenchymal stem cells. Stem cell-seeded bone and cartilage substrates and methods of preparing such substrates are described in published application US 2010/0124776 and in U.S. application Ser. No. 12/965,335, the contents of each of which are incorporated by reference herein.

In some embodiments, perforations (e.g., microperforations or apertures) can operate to facilitate the passage or infiltration of cryopreservatives within and throughout the tissue construct. For example, a cryopreservation protocol may include using a laser to bore perforations (e.g., 100 micron diameter perforations or smaller) within a cartilage sheet (e.g., through channels, tiles, and other portions of the construct). Such perforations can allow a cryopreservative to quickly infiltrate otherwise solid tiles. Hence, the perforations can not only allow for more cells to migrate out and for nutrients to flow from beneath or otherwise through, but can also allow for enhanced cryopreservation of cartilage constructs or sheets. Further, using this approach, large pieces of cartilage constructs can be cryopreserved, and perforation can operate to help maintain suitable temperature gradients for cryopreservation, as well as help facilitate a rapid infiltration of cryopreservative into the cartilage, thus minimizing the duration of contact time between the cryopreservative and the cells until the cryopreservation state is reached. Thus, mosaic cartilage constructs of the present invention can be produced which have a long shelf life and which can be easily stored.

Quantifying Viable Chondrocytes and Characterizing Cartilage Compositions

The mosaic cartilage compositions of the present invention can be characterized with respect to the average number of chondrocytes in the tiles, the average chondrocyte viability in the tiles, or other cartilage characteristics or properties.

In some embodiments, the mosaic cartilage composition comprises cartilage tiles having an average chondrocyte viability of at least 50%, at least 55%, at least 60%, at least 65%, at least 70%, at least 75%, at least 80%, at least 85% or higher. In some embodiments, the composition comprises cartilage tiles having at least about 50,000, at least about 60,000, at least about 70,000, at least about 80,000, at least about 90,000, at least about 100,000, at least about 150,000, at least about 200,000, at least about 250,000, at least about 300,000, at least about 350,000, at least about 400,000, at least about 450,000, at least about 500,000, at least about 550,000, at least about 600,000, at least about 650,000, at least about 700,000, at least about 750,000, at least about 800,000, at least about 850,000, at least about 900,000, at least about 950,000, or at least about 1 million viable chondrocytes per cubic centimeter (cc). In some embodiments, the average chondrocyte viability or the amount of chondrocytes per cc is measured on day 1 following from the day of cutting.

The amount of chondrocytes in the cartilage tiles can be measured by any of a number of cell counting assays. For example, in some embodiments, a Trypan Blue assay or a Presto Blue assay is used to quantify the number of chondrocytes in the cartilage tiles. In some embodiments, the cartilage tissue is cut into the mosaic cartilage construct on day 0 and then the amount of chondrocytes in the cartilage tiles of the mosaic cartilage construct is measured on day 1. In some embodiments, the amount of chondrocytes and/or cell viability is measured on day 1, day 2, day 3, day 4, day 5, day 6, day 7, day 8, day 9, day 10, day 11, day 12, day 13, or day 14 from the day of cutting. In some embodiments, the amount of chondrocytes and/or cell viability is measured 1 week, 2 weeks, 3 weeks, 4 weeks, 5 weeks, or 6 weeks from the day of cutting. In some embodiments, for determining the amount of chondrocytes in a sample, the sample is subjected to digestion, e.g., with collagenase, in order to isolate chondrocytes for cell count and/or viability testing.

In some embodiments, a Trypan Blue assay is used to evaluate cell count and/or cell viability. The Trypan Blue assay is based upon the principle that viable cells do not take up impermeable dyes such as Trypan Blue, but dead cells are permeable and take up the dye. Typically, Trypan Blue stain is added to a sample, then the sample is mixed. An aliquot of the sample is placed on a cell counter slide and the number of cells is counted. The number of cells per cc is calculated based on the starting cartilage sample size.

In some embodiments, a Presto Blue assay is used to evaluate cell count and/or cell viability. The Presto Blue protocol involves an indirect chondrocyte cell count, using a metabolic assay. The cell count is performed by using a standard curve of known concentrations of chondrocytes to determine the count in the unknown samples. Typically, a 1:10 ratio of PrestoBlue® reagent (Life Technologies, Carlsbad, CA) to cell culture medium is added to a sample so that the sample is covered by the medium. The metabolic activity of the cells changes the color of the medium. After 3 hours incubation, 100 µl aliquots are taken from each sample and added to a multi-well plate for reading in a plate reader.

In some embodiments, a cell counting technique other than the Trypan Blue assay or Presto Blue assay is used to determine chondrocyte cell counts in a cartilage sample. For example, the LIVE/DEAD® stain (Life Technologies, Carlsbad, CA) or the CellTiter-Glo® Luminescent Cell Viability Assay (Promega, Madison, WI) can be used to evaluate cell viability. In some embodiments, a Quant-iT™ DNA Assay Kit (Life Technologies, Carlsbad, CA), such as with PicoGreen, can be used to assess DNA content, thereby determining cell count.

In some embodiments, cell viability can be calculated using the following formula:

(number of live cells/total number of live+dead cells)*100%=viability percentage.

The mosaic cartilage constructs can also be evaluated for characteristics of or chondrocyte outgrowth. For example, the mosaic cartilage constructs can be cultured for a period of time (e.g., 1, 2, 3, 4, 5, or 6 weeks) and then assayed for one or more characteristics of chondrocyte outgrowth, such as glycosaminoglycan production, the presence of collagen, or the presence of one or more cartilage-specific biomarkers. In some embodiments, the mosaic cartilage construct is from an adult donor, and the mosaic cartilage construct exhibits one or more characteristics of chondrocyte outgrowth, including but not limited to glycosaminoglycan production, collagen content, or cartilage-specific biomarker expression, that is comparable to those characteristics obtained from a mosaic cartilage construct from a juvenile donor and cultured under the same conditions.

In some embodiments, the mosaic cartilage construct exhibits glycosaminoglycan (GAG) production after being cultured for a period of time (e.g., as described herein in the Examples section). Chondrocytes function in part by producing GAGs and other components of the cartilaginous extracellular matrix. Hence, it is possible to evaluate the chondrocyte activity of cartilage tissue by observing glycosaminoglycan production. The glycosaminoglycan content can be measured, for example, using a dimethylmethylene blue (DM:MB) assay or using Alcian Blue staining. In some embodiments, the levels of sulfated GAGs (sGAGs) are measured. sGAGS are an important component of healthy cartilage and can decrease with age and lead to the development of osteoarthritis. sGAGs can be measured, for example, using a commercially available sGAG Assay Kit (Kamiya Biomedical Company, Seattle, WA).

In some embodiments, the mosaic cartilage construct exhibits collagen production after being cultured for a period of time (e.g., as described herein in the Examples section). Collagen production and collagen content can be measured, for example, using a hydroxyproline assay (BioVison, Milpitas, CA). Collagen production and collagen content can also be measured using an immunoassay (e.g., immunohistochemistry or an immunosorbent assay, e.g., ELISA assay), including but not limited to a Collagen Type II Antibody Staining Protocol.

IV. Methods of Manufacturing Cartilage Compositions

In another aspect, methods of manufacturing cartilage compositions are provided. In some embodiments, the method comprises:
  obtaining cartilage tissue from a human cadaveric donor;
  cutting a plurality of channels or perforations into the cartilage tissue, thereby forming a cartilage sheet comprising a plurality of interconnected tiles that are separated by the channels; and
  suspending the cartilage sheet in a biocompatible medium.

In some embodiments, the cartilage tissue is harvested from an adult cadaveric donor. In some embodiments, the cartilage tissue is harvested from an adult cadaveric donor that is between the ages of 15 and 45 at the time of the donation. In some embodiments, the cartilage tissue is harvested from a juvenile cadaveric donor. Tissue can be harvested from any cartilaginous region of the cadaveric donor. In some embodiments, cartilage is harvested from the knee joint of the donor or from a long bone. In some embodiments, articular cartilage is harvested from the donor. In some embodiments, the cartilage that is obtained from the donor is sliced to a thickness of about 0.25 mm to about 5 mm (e.g., about 0.25 mm, about 0.5 mm, about 0.75 mm, about 1 mm, about 1.5 mm, about 2 mm, about 2.5 mm, about 3 mm, about 3.5 mm, about 4 mm, about 4.5 mm, or about 5 mm, or from about 0.5 mm to about 2 mm) before the cutting step.

The interconnected cartilage tiles can be cut into circles, squares, rectangles, triangles, ovals, polygons, zig-zags, irregular shapes, and the like, or other desired shape or combination of shapes. In some embodiments, the tiles are substantially uniform in size and/or shape. In some embodiments, the cartilage sheet comprises tile having different sizes and/or shapes.

In some embodiments, the cutting step comprises cutting a plurality of channels into the cartilage tissue, wherein each of the plurality of channels has a depth that is less than the maximum thickness of the cartilage tissue. In some embodiments, the channels have a depth that is less than the maximum thickness of the cartilage sheet (e.g., less than the thickness of the cartilage tissue and/or the thickness of the tiles). In some embodiments, the channels have a depth of about 0.2 mm, about 0.3 mm, about 0.4 mm, about 0.5 mm, about 0.6 mm, about 0.7 mm, about 0.8 mm, about 0.9 mm, about 1 mm, about 1.5 mm, about 2 mm, about 2.5 mm, about 3 mm, about 3.5 mm, or about 4 mm. In some embodiments, the cartilage that is beneath the channels has a thickness of less than about 0.25 mm, e.g., less than about 0.2 mm, about 0.15 mm, about 0.1 mm, about 0.09 mm, about 0.08 mm, about 0.07 mm, about 0.06 mm, about 0.05 mm, about 0.04 mm, about 0.03 mm, about 0.02 mm, or about 0.01 mm.

In some embodiments, the cutting step comprises cutting a plurality of perforations into the cartilage. Perforations can include, for example, microperforations, bores, apertures, and the like). In some embodiments, the perforations are microperforations. In some embodiments, the perforations are apertures. In some embodiments, perforations may be on the order of tens of microns in dimension, or less. In some embodiments, perforations may be on the order of millimeters in dimension, or less. For example, in some embodiments, the perforations have an average diameter of about 5 microns, about 10 microns, about 15 microns, about 20 microns, about 25 microns, about 30 microns, about 35 microns, about 40 microns, about 45 microns, about 50 microns, about 60 microns, about 70 microns, about 80 microns, about 90 microns, or about 100 microns.

In some embodiments, the cutting step comprises cutting a plurality of channels into the cartilage tissue, and further comprises cutting perforations in the cartilage beneath one or more of the channels.

In some embodiments, the cartilage tissue is cut into tiles having an average length and/or an average width from about 0.5 mm to about 3 mm (e.g., about 0.5 mm, about 0.6 mm, about 0.7 mm, about 0.8 mm, about 0.9 mm, about 1 mm, about 1.5 mm, about 2 mm, about 2.5 mm, or about 3 mm). In some embodiments, the cartilage tissue is cut into tiles having an average diameter from about 0.5 mm to about 3 mm (e.g., about 0.5 mm, about 0.6 mm, about 0.7 mm, about 0.8 mm, about 0.9 mm, about 1 mm, about 1.5 mm, about 2 mm, about 2.5 mm, or about 3 mm).

In some embodiments, the cartilage tissue is cut into a sheet having a length and/or a width of about 4 mm, about 5 mm, about 6 mm, about 7 mm, about 8 mm, about 9 mm, about 10 mm, about 15 mm, about 20 mm, about 25 mm, about 30 mm, about 35 mm, about 40 mm, about 45 mm, about 50 mm, about 60 mm, about 70 mm, about 80 mm, about 90 mm, or about 100 mm. In some embodiments, the cartilage tissue is cut into a sheet having a diameter of about 4 mm, about 5 mm, about 6 mm, about 7 mm, about 8 mm, about 9 mm, about 10 mm, about 15 mm, about 20 mm, about 25 mm, about 30 mm, about 35 mm, about 40 mm, about 45 mm, about 50 mm, about 60 mm, about 70 mm, about 80 mm, about 90 mm, or about 100 mm.

In some embodiments, the cartilage tissue is cut by hand. In some embodiments, the cartilage tissue is cut using a cutting mechanism. In some embodiments, the cutting mechanism is a laser cutting apparatus, a mechanical blade, a manual cutting apparatus, a manual pressing apparatus, or the like. In some embodiments, the cutting mechanism comprises a pneumatic press, such as an air press or an oil press, or a screw press.

In some embodiments, the cartilage tissue is cut using a laser cutting apparatus. For example, in some embodiments, the laser cutting apparatus is a laser engraver. Non-limiting examples of suitable engraving lasers include $CO_2$ engraving lasers, such as the Epilog Zing 30 Watt $CO_2$ engraving laser. In some embodiments, the cutting step comprises cutting the cartilage tissue with the laser cutting apparatus at a speed from about 10% to about 55% (e.g., about 10%, about 15%, about 20%, about 25%, about 30%, about 35%, about 40%, about 45%, about 50%, or about 55%), a power from about 0% to about 65% (e.g., about 0%, about 1%, about 2%, about 5%, about 10%, about 15%, about 20%, about 25%, about 30%, about 35%, about 40%, about 45%, about 50%, about 55%, about 60%, or about 65%), and a frequency from about 10 Hz to about 2600 Hz (e.g., about 10 Hz, about 20 Hz, about 30 Hz, about 40 Hz, about 50 Hz, about 60 Hz, about 70 Hz, about 80 Hz, about 90 Hz, about 100 Hz, about 150 Hz, about 200 Hz, about 250 Hz, about 300 Hz, about 350 Hz, about 400 Hz, about 450 Hz, about 500 Hz, about 550 Hz, about 600 Hz, about 650 Hz, about 700 Hz, about 750 Hz, about 800 Hz, about 850 Hz, about 900 Hz, about 950 Hz, about 1000 Hz, about 1100 Hz, about 1200 Hz, about 1300 Hz, about 1400 Hz, about 1500 Hz, about 1600 Hz, about 1700 Hz, about 1800 Hz, about 1900 Hz, about 2000 Hz, about 2100 Hz, about 2200 Hz, about 2300 Hz, about 2400 Hz, about 2500 Hz, or about 2600 Hz). In some embodiments, the cutting step comprising cutting the cartilage tissue with the laser cutter at a speed from about 10% to about 50%, a power from about 0% to about 45%, and a frequency from about 10 Hz to about 2400 Hz. In some embodiments, the cutting step comprising cutting the cartilage tissue with the laser cutter at a speed from about 15% to about 55%, a power from about 2% to about 65%, and a frequency from about 200 Hz to about 2600 Hz. Suitable speeds, powers, and frequencies for cutting the cartilage tissue are shown in Table 1.

In some embodiments, on average at least 50% of the chondrocytes in the cartilage composition are viable. In some embodiments, an average at least 50%, at least 55%, at least 60%, at least 65%, at least 70%, at least 75%, at least 80%, at least 85% or more of the chondrocytes in the cartilage composition are viable. In some embodiments, the cartilage particles comprise at least about 50,000, at least about 60,000, at least about 70,000, at least about 80,000, at least about 90,000, at least about 100,000, at least about 150,000, at least about 200,000, at least about 250,000, at least about 300,000, at least about 350,000, at least about 400,000, at least about 450,000, at least about 500,000, at least about 550,000, at least about 600,000, at least about 650,000, at least about 700,000, at least about 750,000, at least about 800,000, at least about 850,000, at least about 900,000, at least about 950,000, or at least about 1 million viable chondrocytes per cubic centimeter (cc). In some embodiments, the average chondrocyte viability or the amount of chondrocytes per cc is measured on day 1 following from the day of cutting. The amount of chondrocytes and/or number of viable chondrocytes in a cartilage sample can be measured as described herein, for example as described in Section III above.

Further Processing Steps

In some embodiments, following the cutting step, the mosaic cartilage composition is not subjected to an additional processing step prior to suspending the cartilage composition in the biocompatible carrier. In some embodiments, following the cutting step, the mosaic cartilage composition can be subjected to one or more additional processing steps prior to suspending the cartilage composition in the biocompatible carrier. In some embodiments, the cartilage composition is washed with a saline solution. In some embodiments, the cartilage composition is treated with one or more enzymes that promote the release of chondrocyte cells from cartilage matrix. For example, collagenase can be applied to help release chondrocyte cells from the cartilage matrix of the composition. In some embodiments, the cartilage composition is mixed with collagenase and/or pronase and incubated in a growth medium such as Dulbecco's Modified Eagle's Medium (DMEM) for a suitable length of time for releasing the chondrocytes.

In some embodiments, the cartilage composition is combined with demineralized bone matrix. For example, in some embodiments the cartilage composition is combined with demineralized bone matrix at a ratio of about 4:1, about 3:1, about 2:1, or about 1:1 demineralized bone matrix:cartilage composition). Demineralized bone matrix can be prepared, e.g., by subjecting a bone substrate to acid, e.g., hydrochloric acid (HCl). Demineralized bone matrix is also commercially available.

In some embodiments, the cartilage composition is combined with cells such as stem cells. In some embodiments, the cartilage composition is combined with a bone or cartilage substrate that is seeded with stem cells. For example, in some embodiments, the cartilage composition is combined with a bone or cartilage substrate (e.g., cortical and/or cancellous bone substrate, demineralized cortical and/or cancellous bone substrate, an osteochondral substrate, or a cartilage substrate) that is seeded with mesenchymal stem cells. Stem cell-seeded bone and cartilage substrates and methods of preparing such substrates are described in U.S. 2010/0124776 and U.S. application Ser. No. 12/965,335, the contents of each of which are incorporated by reference herein.

In some embodiments, at least a portion of the cartilage composition is combined with a biological adhesive. Suitable biological adhesives include, but are not limited to, fibrin, fibrinogen, thrombin, fibrin glue (e.g., TISSEEL), polysaccharide gel, cyanoacrylate glue, gelatin-resorcin-formalin adhesive, collagen gel, synthetic acrylate-based adhesive, cellulose-based adhesive, MATRIGEL® (BD Biosciences, San Jose, CA), laminin, elastin, proteoglycans, and combinations thereof.

In some embodiments, the cartilage composition is suspended in a biocompatible carrier. In some embodiments, the biocompatible carrier comprises a buffered solution (e.g., an aqueous buffered solution). In some embodiments, the biocompatible carrier comprises a cryopreservation medium. In some embodiments, the cryopreservation medium comprises dimethyl sulfoxide (DMSO) and serum. In some embodiments, the biocompatible carrier comprises one or more cryoprotective agents such as, but not limited to, glycerol, DMSO, hydroxyethyl starch, polyethylene glycol, propanediol, ethylene glycol, butanediol, or polyvinylpyrrolidone.

V. Therapeutic Uses of Cartilage Compositions

The mosaic cartilage compositions described herein can be used to treat subjects in need thereof. Without being bound to a particular theory, it is believed that the methods of cutting cartilage described herein can facilitate or enhance the migration of cells out of the cartilage. For example, the cutting of channels and/or perforations onto the surface of cartilage tissue to form interconnected tiles creates a construct having increased surface area relative to a cartilage tissue lacking said channels. This increased surface area can increase or enhance the migration of chondrocytes out of the cartilage tissue relative to the amount of chondrocyte migration in an uncut cartilage tissue. Additionally, the channels and/or perforations can operate to allow nutrients to transfuse easily within, throughout, and across the cartilage construct at an injury site, and thus may contribute to enhanced regeneration and healing.

When the mosaic cartilage compositions as described herein are administered to a subject, the chondrocytes within the cartilage sheet can migrate out of the sheet and carry out repair and regeneration functions. For example, the chondrocytes can reproduce and form new cartilage via chondrogenesis. In this way, a mosaic cartilage composition which is applied to a site within a patient can be used to treat cartilage and/or bone defects. For example, chondrocytes from the mosaic cartilage composition can reproduce and generate new cartilage in situ. The newly established chondrocyte population and cartilage tissue can fill defects, and integrate with existing native cartilage and/or subchondral bone at the treatment site.

In some embodiments, the mosaic cartilage compositions described herein (e.g., a composition comprising a cartilage sheet comprising a plurality of interconnected tiles and a biocompatible carrier) are administered to a subject having a bone or cartilage defect. In some embodiments, the mosaic cartilage composition is administered at a site of defect in cartilage, bone, ligament, tendon, meniscus, joint, or muscle. In some embodiments, the subject has a degenerative defect or injury. In some embodiments, the subject has a traumatic defect or injury. In some embodiments, the subject has osteoarthritis. In some embodiments, the subject has a muscle defect.

In some embodiments, the mosaic cartilage compositions described herein are administered to a subject to repair cartilage or promote cartilage growth or regeneration in the subject. In some embodiments, the mosaic cartilage composition is administered to a joint (e.g., knee joint), to bone (e.g., femur or humerus), or to cartilage.

In some embodiments, the mosaic cartilage compositions described herein are administered to a subject having soft tissue defects, for the repair and regeneration thereof. In some embodiments, the composition is administered to a ligament, tendon, or muscle. In some embodiments, the soft tissue defect is a sprain, strain, contusion, or stress injury to a ligament, tendon, or muscle.

In some embodiments, a mosaic cartilage composition as described herein is administered locally to the subject. In some embodiments, the composition is surgically implanted in the subject. In some embodiments, the composition is administered in a minimally invasive procedure, e.g., arthroscopy.

In some embodiments, a mosaic cartilage composition as described herein is provided to a user (e.g., a physician or a surgeon) as a larger sheet and can be broken into smaller pieces by the user to an appropriate size to suit the size of the defect (e.g., cartilage defect) being treated. For example, a cartilage construct can be broken or separated into two pieces along one or more channels of the construct, or along a perforated section of the construct.

VI. Kits

In still another aspect, kits comprising a mosaic cartilage composition as described herein are provided. In some embodiments, the kit comprises a mosaic cartilage composition comprising a cartilage sheet comprising a plurality of interconnected tiles; and a biocompatible carrier.

In some embodiments, the kits are used for treating a subject having a defect in cartilage, bone, ligament, tendon, meniscus, joint, or muscle. In some embodiments, the kits are used for treating a subject having a degenerative defect or injury cartilage, bone, ligament, tendon, meniscus, joint, or muscle; a subject having a traumatic defect or injury cartilage, bone, ligament, tendon, meniscus, joint, or muscle; or a subject having osteoarthritis.

In some embodiments, a kit comprises a mosaic cartilage composition as described herein packaged in a container for storage and/or shipment. In some embodiments, the kit further comprises instructions for administering the composition.

In some embodiments, a kit comprises a mosaic cartilage composition comprising a cartilage sheet comprising a plurality of interconnected tiles as described herein, optionally along with biological adhesive components (e.g., fibrinogen and thrombin, for a fibrin glue). In some embodiments, cartilage particles and biological adhesive (e.g., fibrin glue) components are packaged separately, and a surgeon or user adds the fibrin glue to the surgery site prior to placement of the cartilage. In some embodiments, the biological adhesive (e.g., fibrin glue) is combined with the cartilage composition prior to administration at the treatment site.

In some instances, a kit comprises the packaged cartilage composition with bone and/or stem cell components. For example, in some embodiments, a kit comprises a cartilage composition with demineralized bone matrix. In some embodiments, a kit comprises a cartilage composition with cells (e.g., stem cells). In some embodiments, a kit comprises a cartilage composition with a bone or cartilage substrate seeded with cells (e.g., adipose derived mesenchymal adult stem cells combined with a bone substrate, as described in U.S. 2010/0124776, or adipose derived mesenchymal adult stem cells combined with an osteochondral or cartilage substrate, as described in U.S. application Ser. No. 12/965,335).

VII. Examples

The following examples are offered to illustrate, but not to limit, the claimed invention.

Example 1: Laser Cutting to Generate Mosaic Cartilage Sheets

Laser cutting techniques can provide a cost effective approach for the preparation of interconnected mosaic cartilage sheets without sacrificing cell viability. As described below, mosaic cartilage sheets comprising a plurality of interconnected tiles as prepared by laser processing techniques showed cell viability results that were comparable to the cell viability results observed when using manual cutting techniques. The use of laser cutting techniques reduces cost, contamination, and processing time, and additionally allows for increased amounts of donor tissue product to be utilized.

Tissue cutting experiments were performed using an Epilog Zing 30 Watt $CO_2$ engraving laser on sheets of juvenile or adult cartilage to form minced cartilage particles and mosaic cartilage constructs. Table 1 shows the results of the tissue cutting experiments at varying speeds, powers, and frequencies.

TABLE 1

Laser Settings

| Speed (%) | Power (%) | Frequency (Hz) | Result/outcome: |
|---|---|---|---|
| A. Low Range Settings Test: 2 mm square pattern cut, 1 mm thick samples used | | | |
| 30 | 10 | 1350 | Etches tissue, no burning, doesn't cut entirely through (mosaic) |
| 30 | 10 | 1000 | Etches tissue, no burning, doesn't cut entirely through (mosaic) |
| 30 | 10 | 750 | Etches tissue, no burning, doesn't cut entirely through (mosaic) |
| 30 | 8 | 750 | Some browning of tissue, perforations through tissue |
| 25 | 8 | 750 | Completely cut through tissue, some brown edges |
| 25 | 8 | 650 | Completely cut through tissue, some brown edges |
| 25 | 8 | 400 | Completely cut through tissue, no browning |
| 25 | 5 | 400 | Etched tissue, some browning, does not cut entirely through |
| 25 | 5 | 300 | Etched tissue, no browning, does not cut entirely through |
| 20 | 5 | 300 | Etched tissue, no browning, nearly complete full thickness cut |
| 20 | 2 | 300 | Etched tissue, no browning, does not cut entirely through |
| 20 | 0 | 300 | Etched tissue, no browning, etching not very deep |
| 20 | 2 | 200 | Etched tissue, no browning, nearly complete full thickness cut |
| 20 | 2 | 100 | Etched tissue, no browning, nearly complete full thickness cut |
| 20 | 2 | 50 | Etched tissue, no browning, nearly complete full thickness cut |
| 20 | 2 | 25 | Etched tissue, no browning, nearly complete full thickness cut with perforations through tissue |
| 20 | 2 | 10 | Perforations (full thickness) only through tissue no complete etched line |
| 20 | 1 | 10 | Perforations only, not a full thickness cut |
| 20 | 0 | 10 | Perforations only, not a full thickness cut |
| 10 | 0 | 10 | Laser very slow moving, tissue etched with perforations (full thickness), no solid line cut |
| B. High Range Settings Test: 2 mm square pattern cut, 1 mm thick samples used | | | |
| 30 | 30 | 2000 | Some browning of edges, complete cut full thickness cut |
| 35 | 30 | 2000 | Less browning than above settings, complete full thickness cut |
| 35 | 35 | 2000 | Some browning of edges, complete cut full thickness cut |
| 35 | 35 | 2200 | Some browning of edges, complete cut full thickness cut |
| 35 | 40 | 2200 | Some browning of edges, complete cut full thickness cut |
| 35 | 40 | 2400 | Browning of edges, complete full thickness cut |
| 35 | 45 | 2400 | dark brown edges, complete cut through |

Based at least in part upon these findings, it was determined that laser settings at 15-55% speed, 2-65% power, and 200-2600 Hz frequency provide desirable results for producing interconnected mosaic cartilage constructs.

Example 2: Characterization of Articular Cartilage from Adult or Juvenile Donors Fresh cadaveric adult and juvenile articular cartilage tissue samples were processed into minced cartilage particles using either a laser cutting protocol or a hand cutting protocol. The adult donors were between fifteen and thirty six years of age, and the juvenile donors were between the ages of three months and 12 years. For the laser cutting method, the cartilage was shaved into thin slices (e.g., sheets having a thickness of 1-5 mm) using a scalpel, and the sliced sheets were minced into small particles (e.g., 1 mm, 2 mm, and/or 3 mm particles) using an Epilog Zing 30 Watt engraving laser. The laser cutting pattern was designed with a CorelDRAW® graphics software program. The cartilage was minced into square shaped particles, using energy levels and other laser parameters as described in Table 1. During the laser cutting procedure, the cartilage was maintained in a hydrated state. The minced particles were then washed with a phosphate buffered saline (PBS) solution. Cartilage particles were characterized for cell count, cell viability, and chondrocyte growth as described below. Mosaic cartilage compositions can also be prepared, e.g., into 3×3 sheets of 2 mm cartilage tiles as described in Example 3 below, and characterized for cell count, cell viability, and chondrocyte growth.

Using samples having known concentrations of chondrocytes, a standard curve was prepared as shown in FIG. 2. The y-axis represents fluorescence readings from a Countess® automated cell counter, and the x-axis represents the chondrocyte concentration (cells/µl).

Cell Counting, Donors A (Adult) and B (Juvenile), Day One: Some of the harvested chondrocytes were tested for cell count on the day of mincing (day 1) using a Trypan blue staining protocol followed by analysis in a Countess® automated cell counter. Cartilage particles were digested with collagenase to isolate chondrocytes, and that mixture was then filtered through a 105 micron filter to separate any undigested matrix from the isolated cells. For the experiments illustrated by FIGS. 3A and 3B, equal amounts of chondrocyte samples were placed in the individual plate wells for evaluation.

Figure 3A:
FIGS. 3A-3B. Mean fluorescence readings for chondrocyte samples from adult donor A as shown in FIG. 3A and chondrocyte samples from juvenile donor B as shown in FIG. 3B placed in six-well tissue culture plates.
Figure 3B:

As depicted in FIG. 3A, adult donor cartilage tissue that was minced with laser cutting provided a mean fluorescence reading of 21,636 (Std. Dev. 578; CV % 2.67), which corresponds to a cell count of 42,622 chondrocytes/µl, using the standard curve of FIG. 2. The adult donor cartilage tissue that was minced with hand cutting provided a mean fluorescence reading of 24,853 (Std. Dev. 1507; CV % 6.06), which corresponds to a cell count of 52,642 chondrocytes/

μl. As depicted in FIG. 3B, juvenile donor cartilage tissue that was minced with laser cutting provided a mean fluorescence reading of 27,528 (Std. Dev. 2494; CV % 9.06), which corresponds to a cell count of 60,974 chondrocytes/μl. The juvenile donor cartilage tissue that was minced with hand cutting provided a mean fluorescence reading of 41,088 (Std. Dev. 3472; CV % 8.45), which corresponds to a cell count of 103,211 chondrocytes/μl. Based on these results, it was observed that in terms of cell count, there may be no large differences between the laser cutting and hand cutting methods.

FIG. 4 shows mean fluorescence readings as described above. The numbers were calculated using a standard curve and the fluorescence reading from a Presto Blue metabolic assay when evaluated in the plate reader. Six week cell counts were also performed using a Presto Blue assay.

Cell Counting, Donors C to G (Six Week): To compare how chondrocytes from both adult and juvenile cartilage grow out of the cartilage matrix, a 6-week explant study was conducted. Three research-consented adult donors (donors C, E, and G) and two research-consented juvenile donors (donors D and F) were obtained. Samples were cut into sheets approximately 1 mm thick and minced by hand or laser cut into 2 mm cubes and measured into 0.3 ml aliquots. Cartilage particles were placed into plate wells along with TISSEEL fibrin glue (Baxter, Deerfield, IL), which provided a support from which the chondrocytes could grow out of the cartilage samples. No collagenase was used on the cells. Chondrocyte media (Cell Applications, San Diego, CA) was then added and changed twice weekly.

Cell counting was conducted after six weeks using either (A) a Trypan Blue staining protocol followed by analysis in a Countess® automated cell counter, or (B) a Presto Blue staining protocol followed by analysis in a Synergy™ H1 hybrid plate reader. The Presto Blue protocol involves an indirect chondrocyte cell count, using a metabolic assay. The cell count is performed by using a standard curve of known concentrations of chondrocytes to determine the count in the unknown samples. Typically, where the chondrocytes are combined with fibrin, a metabolic assay and hybrid reader can be used to indirectly determine the chondrocyte cell count, by evaluating the metabolic activity. Here, it may be assumed that a majority of the cells (e.g., 95% to 98% or more) are viable.

FIG. 5 shows the live cell number count and viability results for the Trypan Blue protocol, and the live cell count number results for the Presto Blue protocol. As depicted in the Trypan Blue live cell test results, there were 1,052, 167±989,536 of live cells per cc of fresh cartilage using laser cutting, and 375,333±295,846 live cells per cc of fresh cartilage using hand cutting.

Figure 6:
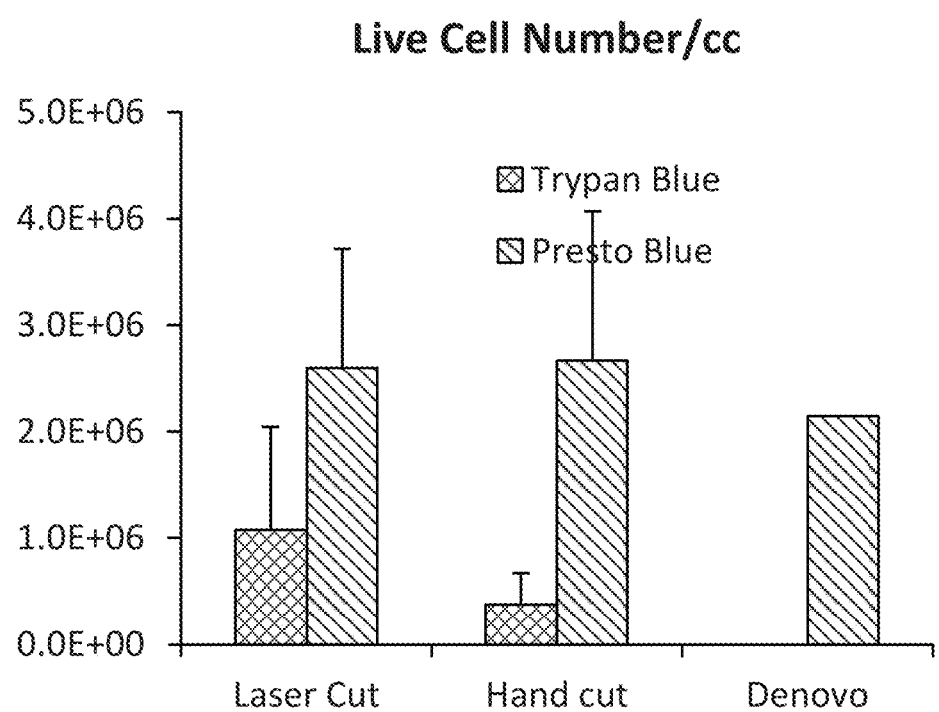
FIG. 6. Graph depicting the live cell count data for Trypan Blue and Presto Blue assays shown in the lower panel of FIG. 5.

FIG. 6 shows the live cell count number results for the Trypan Blue and Presto Blue protocols, and is based on cell count data shown in FIG. 5. With regard to the Trypan Blue and Presto Blue cell count results shown here, a single ANOVA analysis was performed and there was no significant difference using these two methods regarding live cell number.

Figure 7:
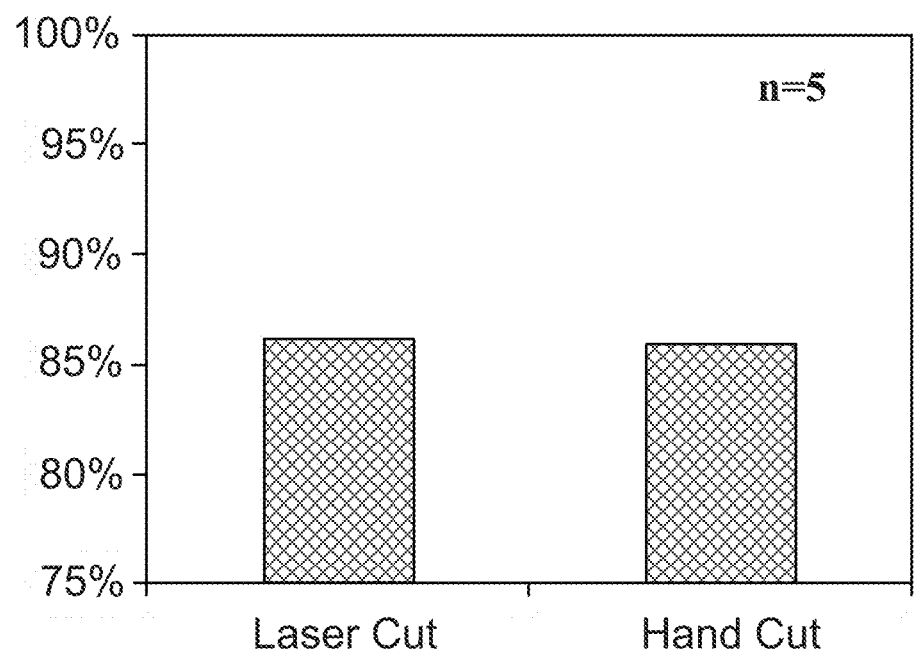
FIG. 7. Trypan Blue cell viability assay at 6 weeks for laser cut and hand cut cartilage particles.

Cell Counting, Donors C to G: FIG. 7 shows day 1 (i.e., one day after cutting) cell viability assay for Donors C to G using the Trypan Blue protocol, which are based on the viability % results depicted in FIG. 5. As depicted here, the average cell viability is about 86% for both laser cut cartilage and hand cut cartilage. Hence, it was observed that cartilage tissue can be minced with laser cutting, without sacrificing cell viability relative to hand cutting methods. With regard to the Trypan Blue viability results shown in FIG. 7, a single ANOVA analysis was performed and there was no significant difference using these two methods regarding cell viability.

Figures 8A, 8B:
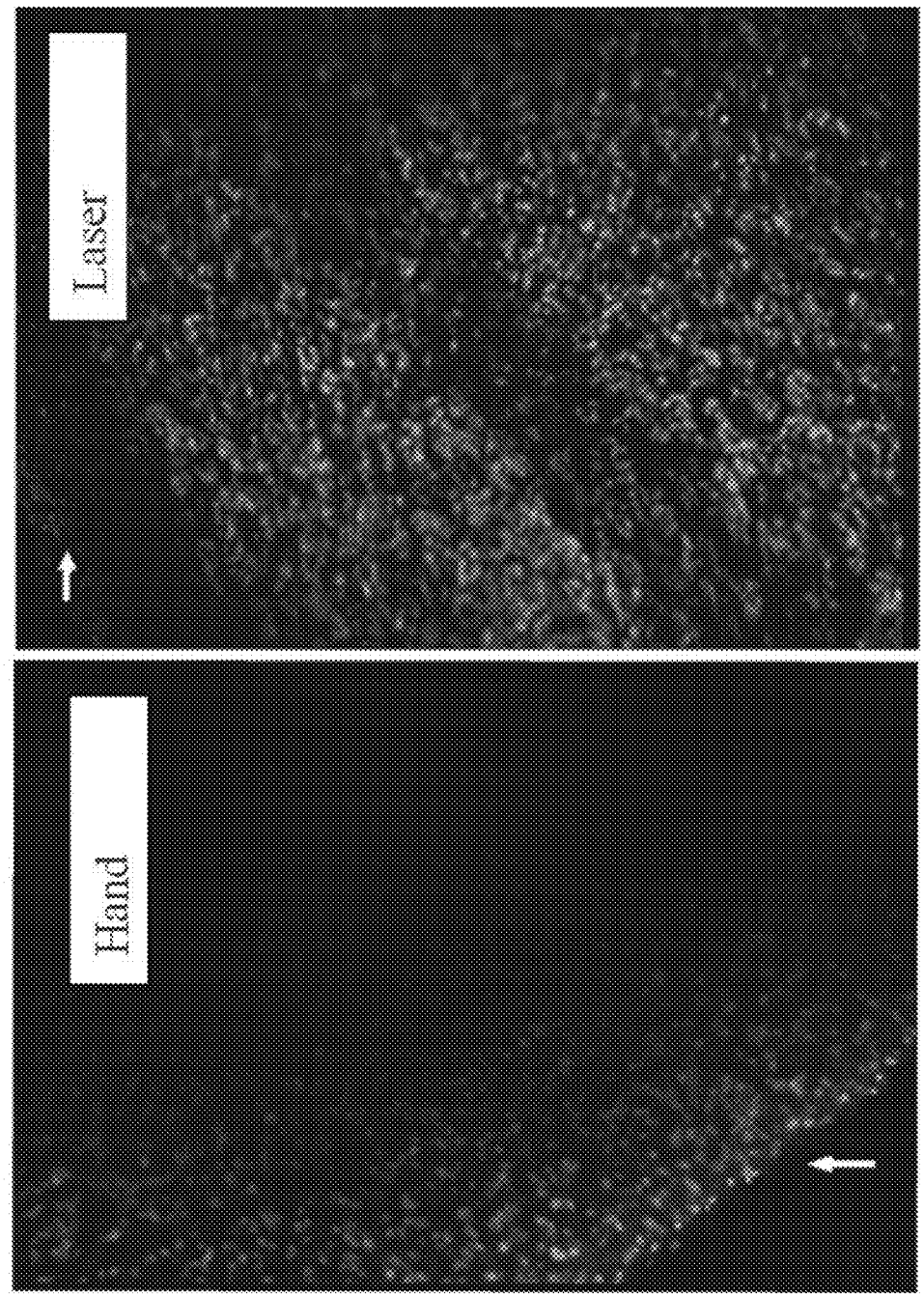
FIGS. 8A-8B. Confocal microscope images depicting tissue edges (white arrow) of hand cut and laser cut cartilage pieces are shown in FIG. 8A and FIG. 8B, respectively. Invitrogen LIVE/DEAD® stain was used on undigested cartilage sample for visualizing cells.

FIGS. 8A and 8B are confocal microscope images depicting tissue edges (white arrow) of hand cut and laser cut (respectively) cartilage pieces. These results indicate that there was not a significant difference of cell viability when comparing laser cut and hand cut cartilage tissue samples. For this study, LIVE/DEAD® stain (Life Technologies, Carlsbad, CA) was used. Briefly, undigested cartilage particles were placed in wells of a 24-well plate. 1 ml PBS was added to each well and 0.5 μl of the red and green dye was then added. The plates were covered with foil and allowed to sit for a minimum of 15 minutes. The cartilage particles were then placed on slides and the images captured by confocal microscopy on the laser setting.

It was also observed that laser cutting could be accomplished more quickly than hand cutting. For example, an equivalent amount of tissue could be minced in 8 hours via manual cutting, versus 0.5 hours via laser cutting. Moreover, it was observed that it was easier to obtain uniformly shaped tissue pieces using laser cutting, as compared with hand cutting.

Figure 9B:
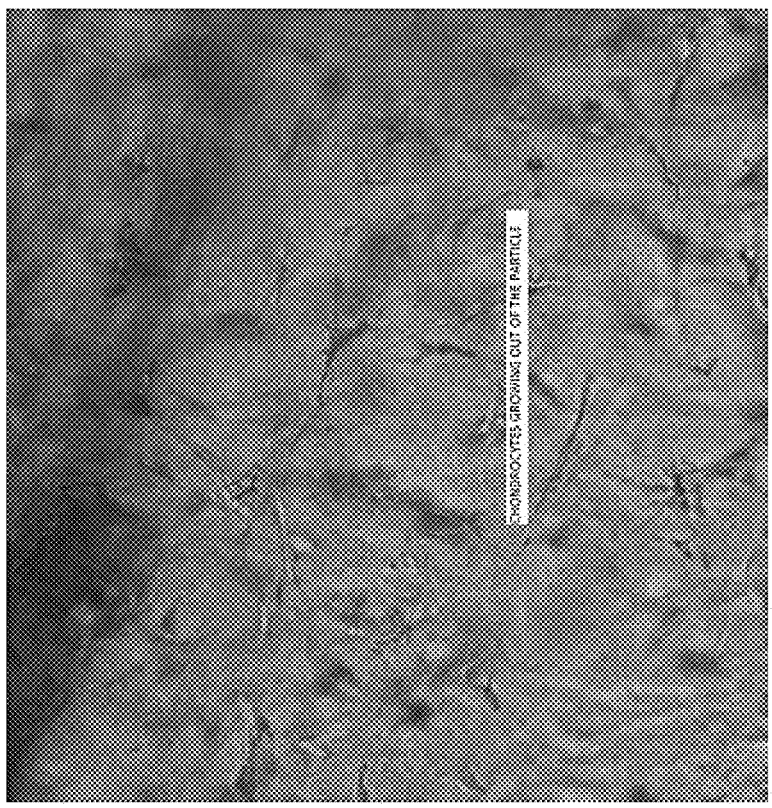
FIGS. 9A and 9B. Photographic images at 4× magnification of chondrocyte cells growing out of hand cut (FIG. 9A) and laser cut (FIG. 9B) adult cartilage particles. Cartilage particles were placed in 12-well culture plates with chondrocyte growth medium containing 10% FBS and 2% antibiotic. The medium was changed twice a week. The plates were cultured under standard cell culture conditions (37° C. incubator with 5% $CO_2$) and the images were obtained at 18 days.
Figure 9A:
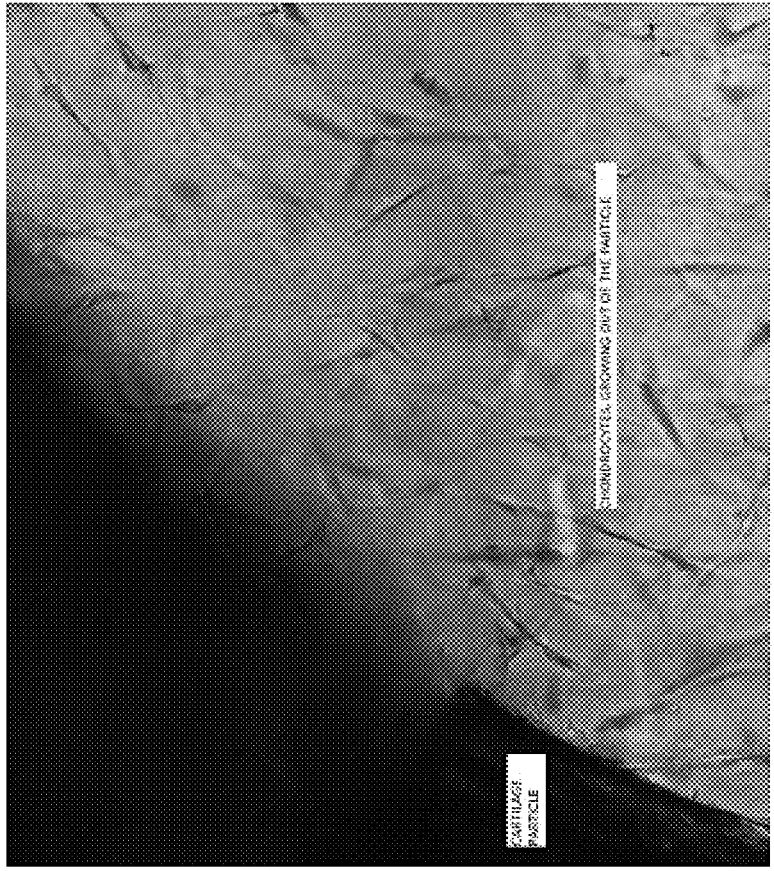
Figure 10:
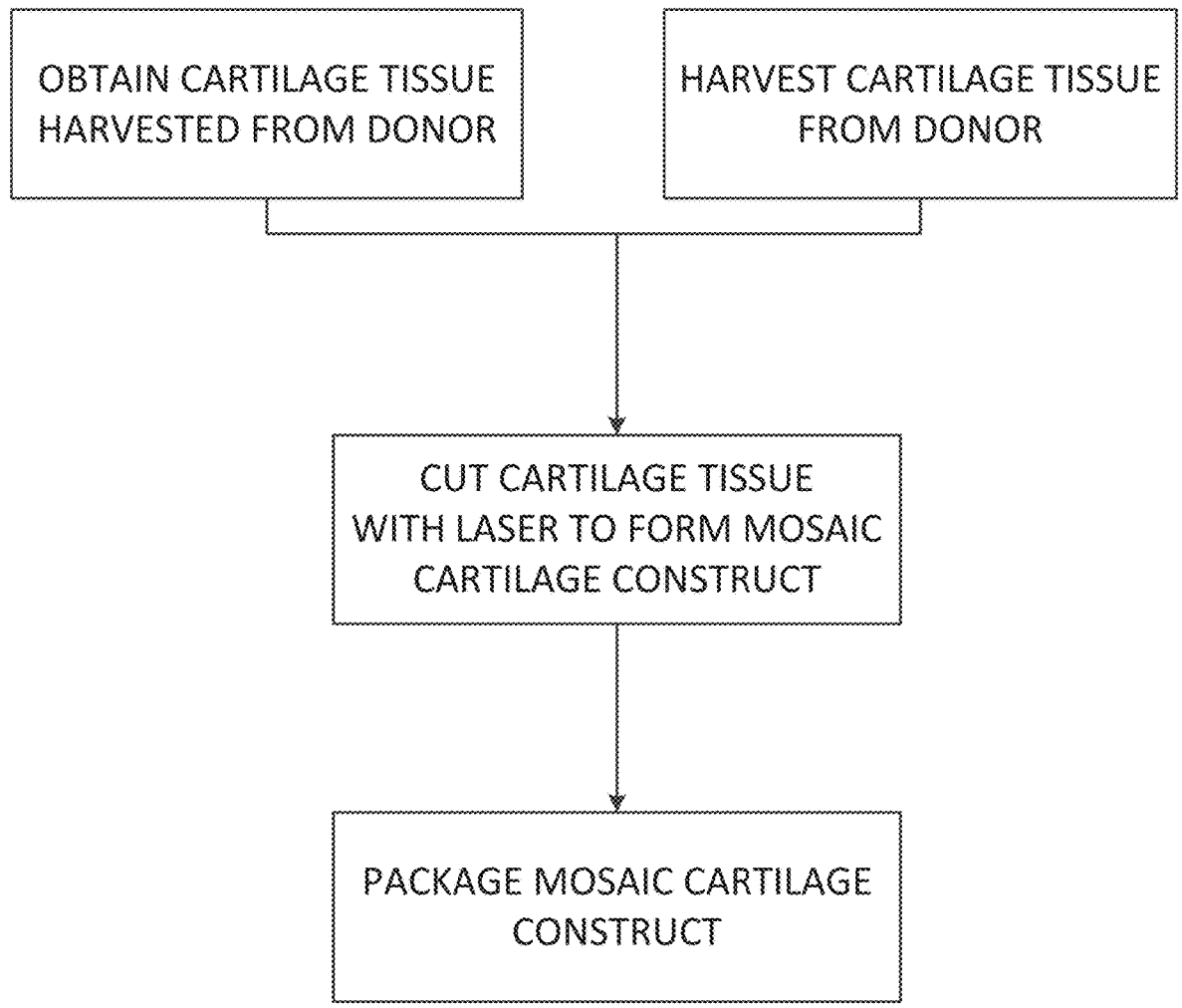
FIG. 10. Schematic of an exemplary manufacturing method for cartilage compositions.
Figure 11A:
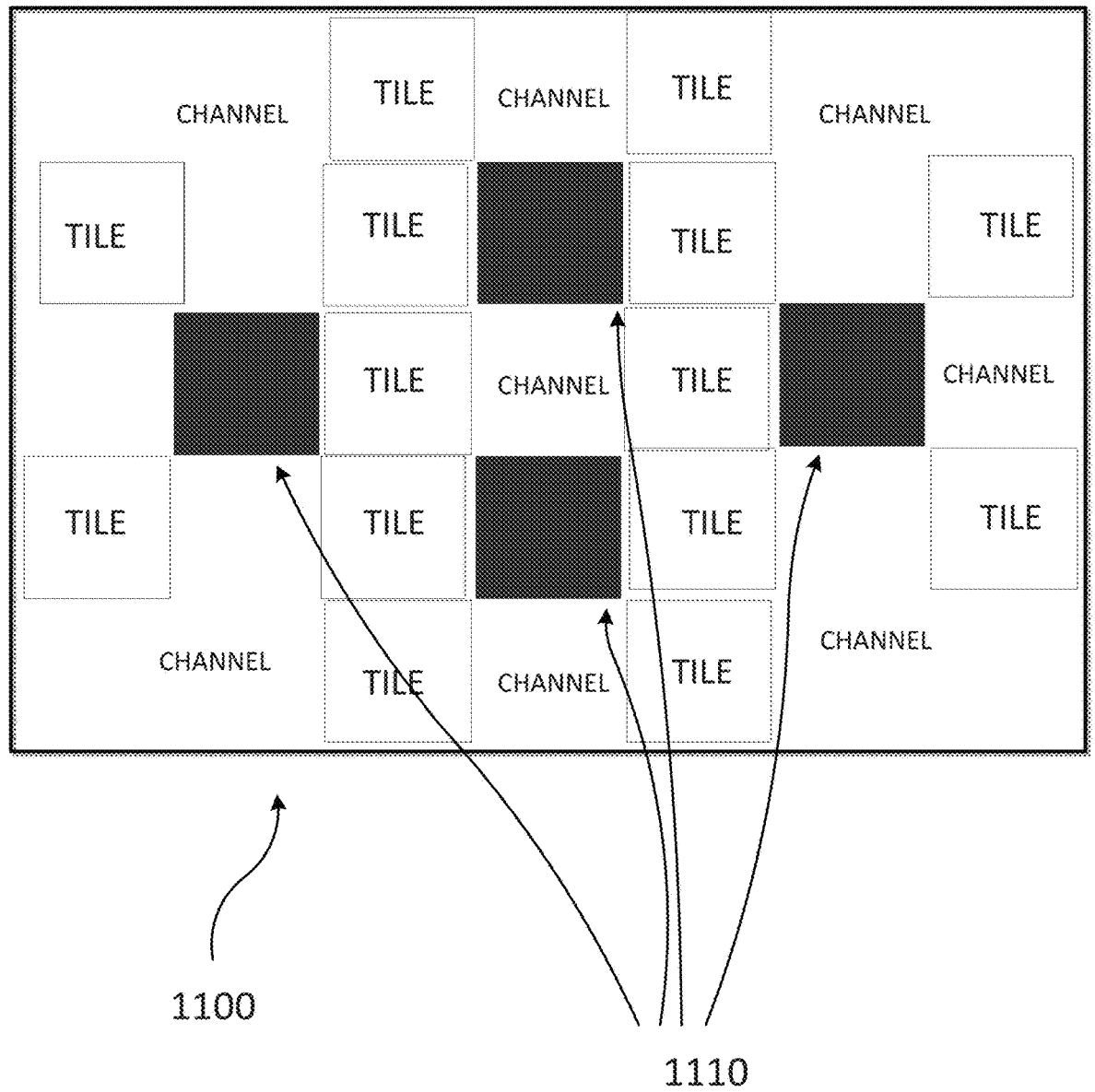
FIGS. 11A-11B.
Figure 11B:
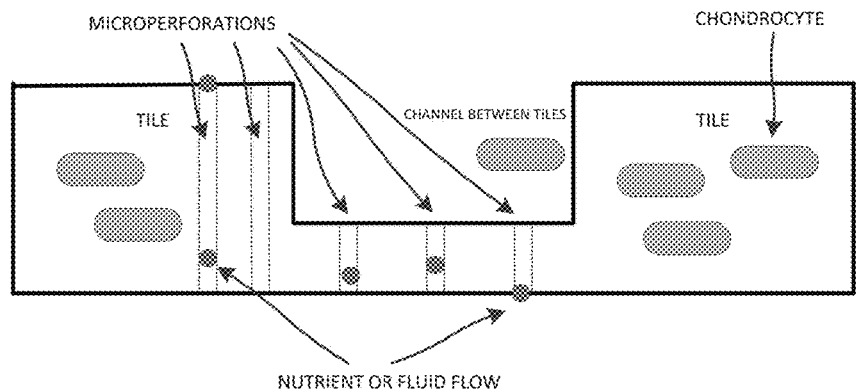

Microscopy Observations At Eighteen Days: FIGS. 9A and 9B provide photographic images of chondrocyte cells growing out of hand cut (FIG. 9A) and laser cut (FIG. 9B) adult cartilage particles. Specifically, cartilage was obtained from an adult donor, and minced with either laser cutting or manual cutting protocols. The minced cartilage particles were placed in 12 well culture plates, using chondrocyte growth medium with 10% FBS and 2% antibiotic. The media was changed twice a week. The plates were cultured in a 37° C. incubator with 5% $CO_2$ (e.g., standard cell culture conditions). The images (4× magnification) were obtained at 18 days. As shown here, chondrocytes were observed to grow out of the minced particles.

It has previously been suggested that adult cartilage is not well suited for use in allogeneic grafts. However, this example demonstrates that adult cartilage constructs, when cultured for a period of time, exhibit comparable chondrocyte outgrowth and matrix production as juvenile cartilage constructs. Thus, cartilage constructs derived from human adult donors or from human juvenile donors can be useful for repairing cartilage defects in subjects in need thereof.

Example 3: 12-Week Explant Study to Characterize Cartilage Samples

To further compare chondrocyte outgrowth and matrix production of mosaic cartilage compositions, a 12-week explant study was performed. Three research consented adult donors and two research consented juvenile donors were obtained. For cell counting, a 1:10 ratio of Presto-Blue® (Life Technologies, Carlsbad, CA) to media was used. Collagen type II immunohistochemistry was performed on samples after the 12 week time point, as well as sulfated glycosaminoglycans (sGAG) assay (Kamiya Biomedical Company, Seattle, WA), hydroxyproline assay (BioVison, Milpitas, CA), and DNA analysis with a Pico Green Assay (Invitrogen, Grand Island, NY). All outcome measures were evaluated using single ANOVA analysis. Significance was considered as $p \leq 0.05$.

Cartilage Explant Protocol

1. Remove media and wash cartilage samples with PBS+ 2% antibiotic.

2. Place tissue on chilled laser plate as flat as possible.
3. Add several drops of PBS+2% antibiotic to tissue to keep moist during cutting, place plate inside laser.
4. Select desired laser template and set laser settings to Speed=50%, Power=30%, and Hz=2000. Select print and press go on the laser.
5. Measure out 0.3 cc of cartilage using 15 ml conical tube with 2.7 mL of medium and bring up to 3 mL. Mosaic cartilage sheets comprising 2 mm squares in a 3×3 (6 mm×6 mm) sheet were formed.
6. Place TISSEL fibrin glue in base of well and add cartilage.
7. After all samples have been added to plate, allow 30 minutes for glue to dry.
8. After cartilage has attached and glue has dried, add 4 mL medium gently to well as to not disturb the cartilage.
9. On day 1, remove medium to run Presto Blue, 1 mL medium+110 μL Presto Blue into each well and incubate for 4.5 hours. Remove medium and Presto Blue and rinse with PBS+2% antibiotic. Replace medium.
10. Change medium twice weekly.
11. Incubate plates. Check for cell explant growth with Presto Blue at weeks 3, 6, 9, and 12.

TABLE 2

Summary of samples

| Assay | Laser cut minced with fibrin glue | Laser cut mosaic with fibrin glue |
|---|---|---|
| Cell count (Presto Blue) | n = 3 | n = 3 |
| Presto Blue DNA assay (cell count) | n = 3 | n = 3 |
| GAG Analysis | n = 2 | n = 2 |

TABLE 3

12 well plate layout (sample designation)

| | | | |
|---|---|---|---|
| Laser Cut minced sample: GAG Analysis, Presto Blue | Laser Cut minced sample: Presto Blue/histology | Mosaic Cut Sample: GAG Analysis, Presto Blue | Mosaic Cut Sample: Presto Blue/histology |
| Laser Cut minced sample: GAG Analysis, Presto Blue | Laser Cut minced sample: Spare in case of contamination | Mosaic Cut Sample: GAG Analysis, Presto Blue | Mosaic Cut Sample: Spare in case of contamination |
| Laser Cut minced sample: GAG Analysis, Presto Blue | EMPTY well or back-up well if enough tissue | Mosaic Cut Sample: GAG Analysis, Presto Blue | EMPTY well or back-up well if enough tissue |

Results

Figure 20:
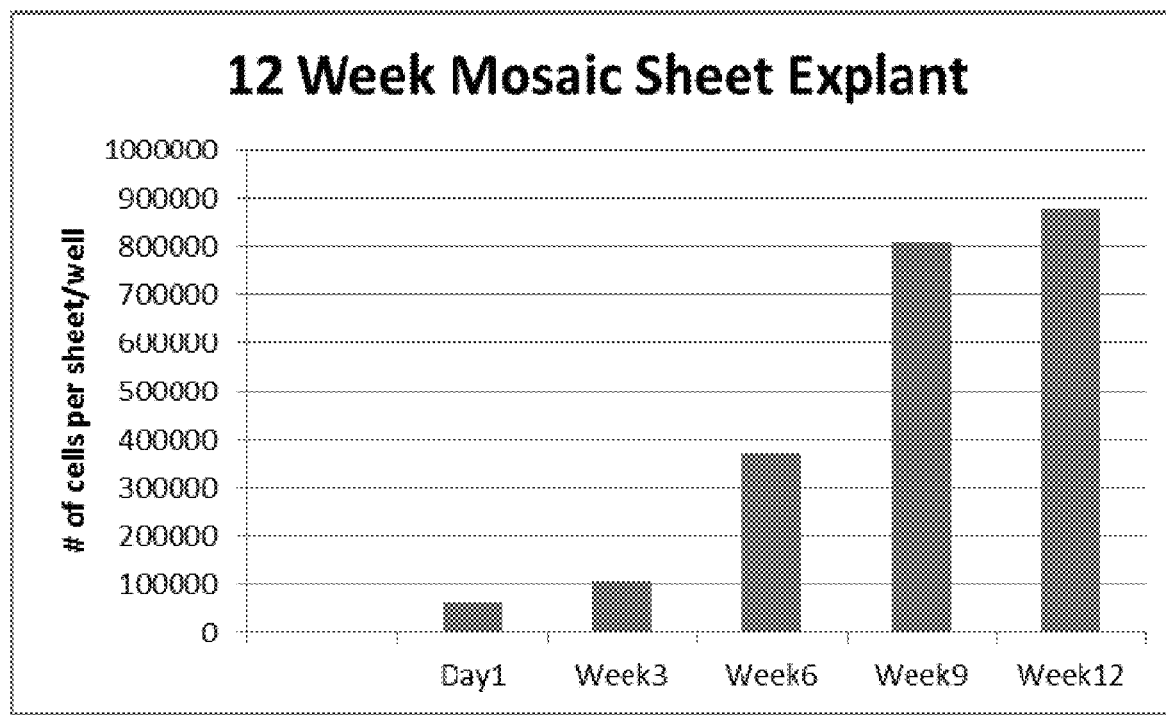
FIG. 20. Graph depicting the average live cell count data, as determined by Presto Blue assays, for adult mosaic cartilage compositions after day 1, week 3, week 6, week 9, and week 12 of culture.

The 12-week study demonstrated that mosaic cartilage compositions exhibited cell outgrowth and matrix production. Mosaic cartilage compositions from adult donors exhibited an increase in the number of cells per sheet/well over the course of the 12-week explant study (FIG. 20), as did mosaic cartilage compositions from juvenile donors (data not shown).

Figure 21:
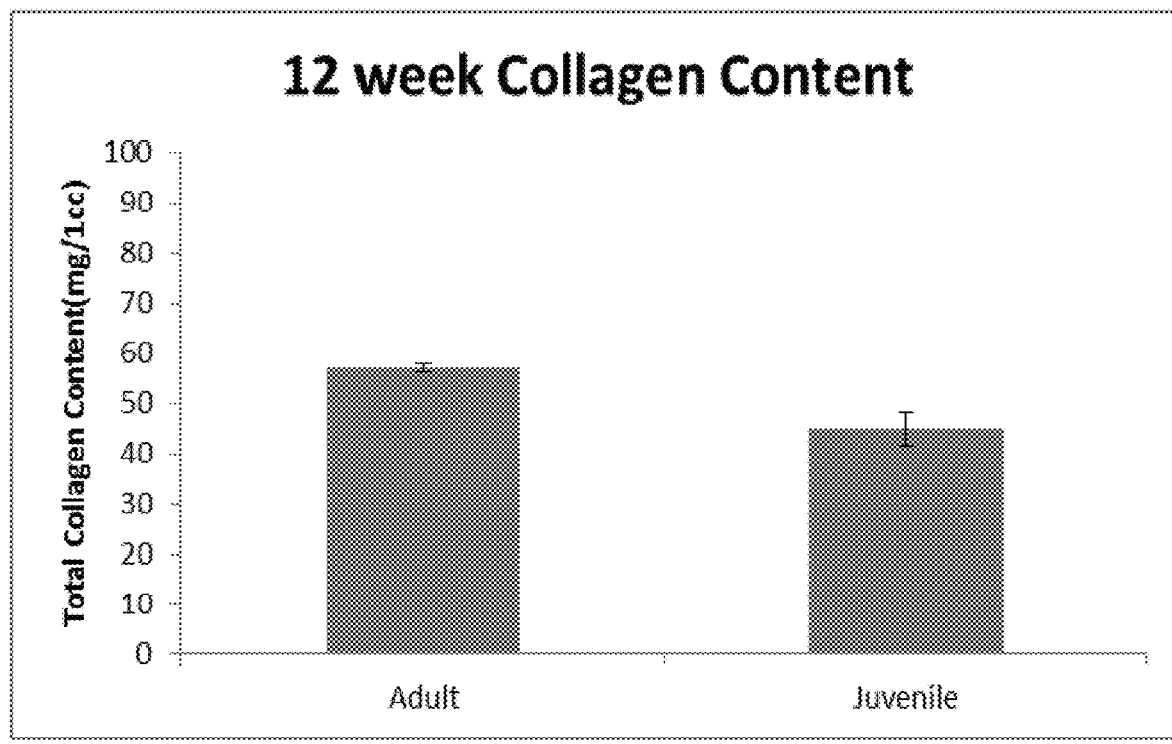
FIG. 21. Comparison of total collagen content (mg/1 cc) in adult and juvenile mosaic cartilage compositions after 12 weeks of culture.

A hydroxyproline assay was used to determine the total collagen content of the explants. As shown in Table 4 and FIG. 21, mosaic cartilage compositions from adult donors had a total collagen content of 57.14±0.72 mg/ml. Juvenile donors had a total of 44.95±3.32 mg/ml, resulting in no statistical difference.

TABLE 4

Results for hydroxyproline and sGAG after 12 weeks of explant

| | Average Result | | Standard Deviation | | | Statistically |
|---|---|---|---|---|---|---|
| Assay | Adult | Juvenile | Adult | Juvenile | P-value | Different? |
| Hydroxyproline (ug/well) | 57.13766 | 44.95186 | 0.716883 | 3.324416 | 0.9 | NO |
| sGAG (ug/well) | 199541 | 197442.6 | 37371.07 | 15857.74 | | NO |

Figure 22:
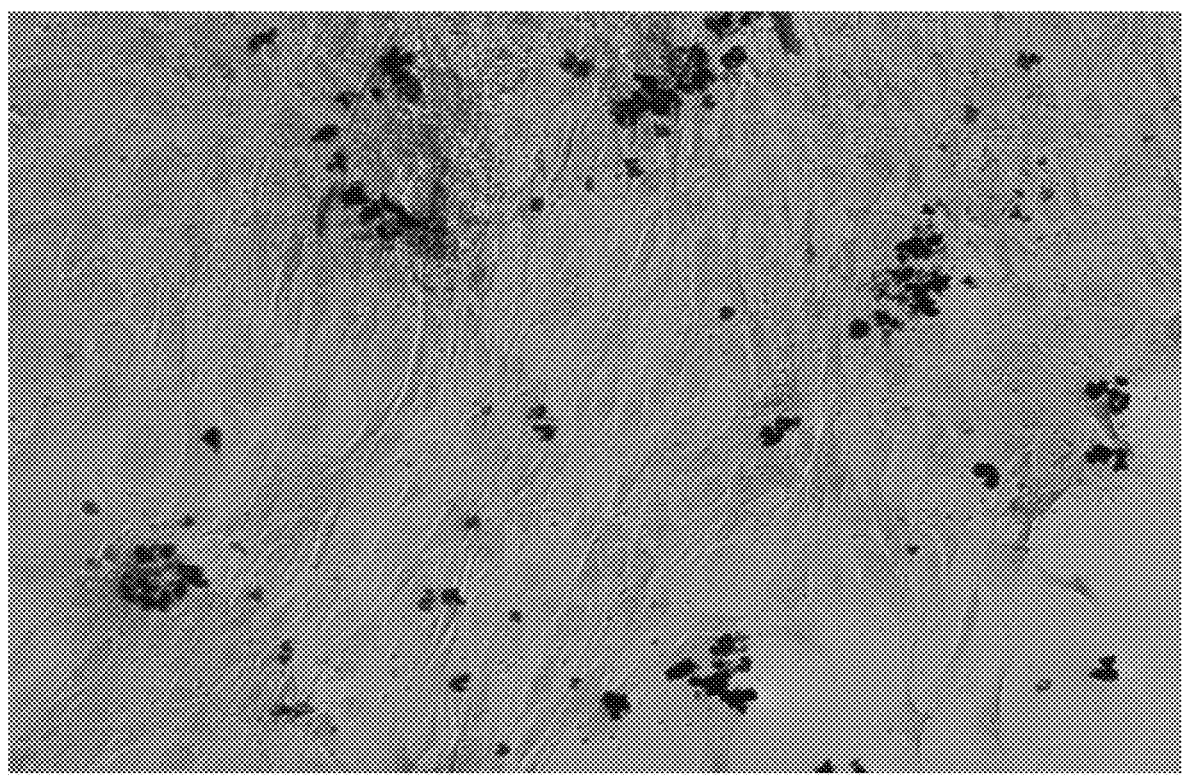
FIG. 22. Sulfated glycosaminoglycan (sGAG) production in an adult mosaic cartilage composition after 12 weeks of culture.

Sulfated glycosaminoglycans (sGAGS) are an important component of healthy cartilage and can decrease with age and lead to the development of osteoarthritis. Average sGAG content for an adult mosaic cartilage sample was 199,541±37,371 ug/ml after 12 weeks of explant, while average sGAG content for a juvenile donor sample was 197,442±15,857 ug/ml after 12 weeks of explant, showing that sGAG content has no statistical difference between samples from adult and juvenile cartilage tissue. sGAG staining of a mosaic cartilage composition from an adult donor after 12 weeks of culturing is shown in FIG. 22.

Figure 23:
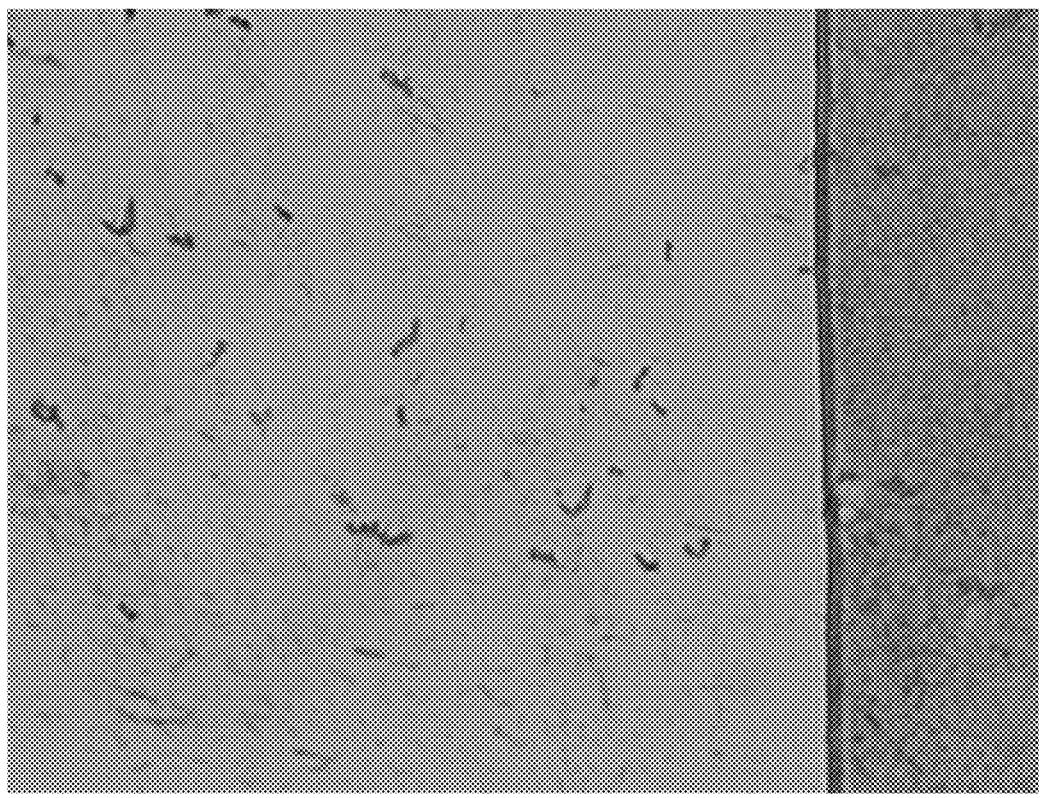
FIG. 23. Immunohistochemistry for type II collagen in an adult mosaic cartilage composition after 12 weeks of culture. Brown staining in the cartilage indicates types II collagen produced by cells that grew out of the cartilage.

Immunohistochemistry was also performed on mosaic cartilage samples after 12 weeks. As shown in FIG. 23, type II collagen was produced by cells that grew out of the mosaic cartilage composition. Type II collagen is important for the production of hyaline cartilage, and the formation of the hyaline cartilage outside of the explant shows that the mosaic cartilage compositions as described herein can be effective in cartilage repair.

Although the foregoing invention has been described in some detail by way of illustration and example for purposes of clarity of understanding, one of skill in the art will appreciate that certain changes and modifications may be practiced within the scope of the appended claims. In addition, each reference provided herein in incorporated by reference in its entirety to the same extent as if each reference was individually incorporated by reference.

What is claimed is:

1. A mosaic cartilage composition comprising:
   a cartilage sheet comprising a plurality of interconnected cartilage tiles that are separated by channels formed in the cartilage sheet, wherein the cartilage sheet comprises seeded viable mesenchymal stem cells; and
   a biocompatible carrier.

2. The mosaic cartilage composition of claim 1, further comprising a bone or cartilage substrate seeded with cells.

3. The mosaic cartilage composition of claim 1, wherein the biocompatible carrier comprises a cryopreservation medium.

4. The mosaic cartilage composition of claim 1, wherein the cartilage sheet has a maximum thickness of about 0.25 mm to about 5 mm.

5. A mosaic cartilage composition comprising:
   a cartilage sheet comprising a plurality of interconnected cartilage tiles, wherein the plurality of interconnected cartilage tiles are partially connected to one or more adjacent tiles; and
   a biocompatible carrier.

6. The mosaic cartilage composition of claim 5, wherein the plurality of interconnected cartilage tiles are partially connected to one or more adjacent tiles by a perforated line.

7. The mosaic cartilage composition of claim 5, wherein the plurality of interconnected cartilage tiles are partially connected to one or more adjacent tiles by a channel.

8. The mosaic cartilage composition of claim 5, wherein the plurality of interconnected cartilage tiles are partially connected to one or more adjacent tiles by one or more apertures.

9. The mosaic cartilage composition of claim 5, wherein the plurality of interconnected cartilage tiles are part of a single piece of cartilage.

10. The mosaic cartilage composition of claim 5, wherein the plurality of interconnected cartilage tiles comprise more than one piece of cartilage.

11. The mosaic cartilage composition of claim 5, wherein the cartilage sheet comprises articular cartilage.

12. The mosaic cartilage composition of claim 5, wherein the cartilage sheet comprises non-decellularized cartilage.

13. The mosaic cartilage composition of claim 5, wherein at least a portion of the cartilage sheet is combined with a bone or cartilage substrate that is seeded with stem cells.

14. The mosaic cartilage composition of claim 5, wherein the biocompatible carrier comprises a cryopreservation medium.

15. The mosaic cartilage composition of claim 5, wherein the cartilage is from a human adult cadaveric donor.

* * * * *

UNITED STATES PATENT AND TRADEMARK OFFICE
CERTIFICATE OF CORRECTION

| | | |
|---|---|---|
| PATENT NO. | : 12,127,943 B2 | Page 1 of 1 |
| APPLICATION NO. | : 17/388388 | |
| DATED | : October 29, 2024 | |
| INVENTOR(S) | : Rorick et al. | |

It is certified that error appears in the above-identified patent and that said Letters Patent is hereby corrected as shown below:

In the Claims

In Column 24, Line 24, in Claim 15, delete "is" and insert -- sheet is --.

Signed and Sealed this
Fourth Day of February, 2025

Coke Morgan Stewart
*Acting Director of the United States Patent and Trademark Office*